(12) United States Patent
Asadi et al.

(10) Patent No.: US 12,060,508 B2
(45) Date of Patent: Aug. 13, 2024

(54) FLUORESCENT DETECTION OF AMINES AND HYDRAZINES AND ASSAYING METHODS THEREOF

(71) Applicant: ILLUMINA, INC., San Diego, CA (US)

(72) Inventors: Ali Asadi, San Diego, CA (US); Jian-Sen Li, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 18/062,492

(22) Filed: Dec. 6, 2022

(65) Prior Publication Data

US 2023/0139797 A1 May 4, 2023

Related U.S. Application Data

(62) Division of application No. 16/316,996, filed as application No. PCT/US2017/054785 on Oct. 2, 2017, now Pat. No. 11,530,352.

(60) Provisional application No. 62/403,421, filed on Oct. 3, 2016.

(51) Int. Cl.
| | |
|---|---|
| *C09K 11/00* | (2006.01) |
| *C07D 209/62* | (2006.01) |
| *C07D 237/26* | (2006.01) |
| *C09K 11/07* | (2006.01) |
| *G01N 21/64* | (2006.01) |
| *G07C 3/14* | (2006.01) |

(Continued)

(52) U.S. Cl.
CPC ............ *C09K 11/07* (2013.01); *C07D 209/62* (2013.01); *C07D 237/26* (2013.01); *G01N 21/6428* (2013.01); *G07C 3/14* (2013.01); *C07D 471/04* (2013.01); *C09K 2211/1022* (2013.01); *G01N 21/314* (2013.01); *G01N 2021/3155* (2013.01)

(58) Field of Classification Search
CPC ...................................................... C09K 11/00
USPC ............................................................ 252/700
See application file for complete search history.

(56) References Cited

U.S. PATENT DOCUMENTS

| | | |
|---|---|---|
| 6,210,891 B1 | 4/2001 | Nyren et al. |
| 6,258,568 B1 | 7/2001 | Nyren |
| 6,266,459 B1 | 7/2001 | Walt et al. |

(Continued)

FOREIGN PATENT DOCUMENTS

| | | |
|---|---|---|
| EP | 0 199 432 | 10/1986 |
| EP | 1437594 B1 | 1/2011 |

(Continued)

OTHER PUBLICATIONS

Magriz et al. "Phthalazin-2-ylidenes as Cyclic Amino Aryl Carbene Ligands in Rhodium(I) and Iridium(I) Complexes" Organometallics 2010, 29, 5941-5945 (Year: 2010).*

(Continued)

*Primary Examiner* — Christine T Mui
*Assistant Examiner* — Emily R. Berkeley
(74) *Attorney, Agent, or Firm* — Knobbe, Martens, Olson & Bear, LLP

(57) ABSTRACT

Provided herein are processes for preparing fluorescent 1-cyano-2-substituted isoindole compounds or N-substituted phthalazinium compounds, comprising reacting an (Continued)

aromatic dialdehyde or aromatic aldehyde-ketone compound with a material that contains primary amino or hydrazine groups, and assaying methods involving the processes thereof.

22 Claims, 4 Drawing Sheets

(51) Int. Cl.
    *C07D 471/04* (2006.01)
    *G01N 21/31* (2006.01)

(56) References Cited

U.S. PATENT DOCUMENTS

| | | | |
|---|---|---|---|
| 6,274,320 | B1 | 8/2001 | Rothberg et al. |
| 6,355,431 | B1 | 3/2002 | Chee et al. |
| 6,465,178 | B2 | 10/2002 | Chappa et al. |
| 6,770,441 | B2 | 8/2004 | Dickinson et al. |
| 6,859,570 | B2 | 2/2005 | Walt et al. |
| 8,597,959 | B2 * | 12/2013 | Jing ................ G01N 33/54393 436/524 |
| 8,951,781 | B2 | 2/2015 | Reed et al. |
| 9,012,022 | B2 | 4/2015 | George et al. |
| 9,297,006 | B2 | 3/2016 | Adessi et al. |
| 11,530,352 | B2 | 12/2022 | Asadi et al. |
| 2009/0026082 | A1 | 1/2009 | Rothberg et al. |
| 2009/0127589 | A1 | 5/2009 | Rothberg et al. |
| 2010/0111768 | A1 | 5/2010 | Banerjee et al. |
| 2010/0137143 | A1 | 6/2010 | Rothberg et al. |
| 2010/0282617 | A1 | 11/2010 | Rothberg et al. |
| 2011/0059865 | A1 | 3/2011 | Smith et al. |
| 2011/0268903 | A1 | 11/2011 | Zhao et al. |
| 2015/0125928 | A1 | 5/2015 | Wong et al. |

FOREIGN PATENT DOCUMENTS

| | | |
|---|---|---|
| WO | WO 00/16101 | 3/2000 |
| WO | WO 00/18957 A1 | 4/2000 |
| WO | WO 00/31148 | 6/2000 |
| WO | WO 00/53812 | 9/2000 |
| WO | WO 00/63437 | 10/2000 |
| WO | WO 01/01143 | 1/2001 |
| WO | WO 01/62982 | 8/2001 |
| WO | WO 03/014392 | 2/2003 |
| WO | WO 03/097810 A2 | 11/2003 |
| WO | WO 2014/142841 | 9/2014 |

OTHER PUBLICATIONS

Carion et al. "Chemical Micropatterning of Polycarbonate for Site-Specific Peptide Immobilization and Biomolecular Interactions" ChemBioChem 2007, 8, 315-322 (Year: 2007).*

"Microsphere Selection Guide", Sep. 1998, Bangs Laboratories, Inc., Fishers, IN (pp. 1-8).

Diaz-Ortiz, et al., "Synthesis, structural determination and dynamic behavior of 2-chloro-4,6-bis (pyrazolylamino)-1,3,5-triazines." Organic and Biomolecular Chemistry, vol. 1, No. 24, Nov. 10, 2003, pp. 4451-4457; p. 4452, col. 1, paragraph 2.

Kricka, LJ et al., "Analytical Ancestry: Firsts in Fluorescent Labeling of Nucleosides, Nucleotides, and Nucleic Acids", Clinical Chemistry, vol. 55, No. 4, Mar. 2009, pp. 670-683.

Padalkar, et al., "Synthesis and characterization of novel 4-( 1-(4-( 4-(4-aminophenyl)-1 Hpyrazol-1-yl)-6-( 4-(diethylamino) phenyl)-1,3,5-triazin-2-yl)-1 H-pyrazol-4-yl)benzenamine fluorescent dye for protein binding", Current Chemistry Letters, vol. 1, No. 1, Jan. 2012, pp. 1-12.

Parrino et al. "Synthesis of isoindolo[1,4]benzoxazinone and isoindolo[1,5] benzoxazepine: two new ring systems of pharmaceutical interest" Tetrahedron 71 (2015) 7332-7338 (Year: 2015).

Shuhendler et al. "A Novel Solid Lipid Nanoparticle Formulation for Active Targeting to Tumor avf33 Integrin Receptors Reveals Cyclic RGD as a Double-Edged Sword" Adv. Healthcare Mater. 2012, 1, 600-608 (Year: 2012).

Wong, et al., "Self-assembly, stability quantification, controlled molecular switching, and sensing properties of an anthracene-containing dynamic [2]rotaxane", Organic and Biomolecular Chemistry, vol. 8, Mar. 19, 2010, 8, 2332-2343.

Xiong, et al., "pKa of adenine 2451 in the ribosomal peptidyl transferase center remains Elusive", RNA, vol. 7, No. 10, Oct. 2001, pp. 1365-1369.

Yang et al., "有机合成 (Organic Synthesis)", East China University of Science and Technology Press, pp. 198-202, 2010.

Zieris, et al., "FGF-2 and VEGF functionalization of starPEGeheparin hydrogels to modulate biomolecular and physical cues of angiogenesis", Biomaterials, vol. 31, Aug. 3, 2010, pp. 7985-7994.

* cited by examiner

FLUORESCENT DETECTION OF AMINES AND HYDRAZINES AND ASSAYING METHODS THEREOF

INCORPORATION BY REFERENCE TO PRIORITY APPLICATIONS

This application is a divisional application of U.S. application Ser. No. 16/316,996, filed Jan. 10, 2019, which is the national phase under 35 U.S.C. § 371 of International Application No. PCT/US2017/054785, filed Oct. 2, 2017, which claims the benefit of priority to U.S. Provisional Application No. 62/403,421, filed Oct. 3, 2016, each which is incorporated by reference in its entirety.

BACKGROUND

Chemical reactions of a non-fluorescent or weakly fluorescent reagent with a substrate to provide a fluorescent product have found applications in the field of analytic chemistry in the past decades. One such reaction involves reacting an aromatic dialdehyde with a primary amine in the presence of a cyanide ion to provide a fluorescent 1-cyano-2-substituted isoindole compound. Another reaction involves reacting an aromatic dialdehyde with a primary hydrazine to provide a fluorescent N-substituted phthalazinium compound. The common aromatic dicarboxaldehydes used in these reactions include o-phthalaldehyde (OPA), naphthalene-2,3-dicarbaldehyde (NDA), anthracene-2,3-dicarbaldehyde (ADA), and 3-(4-carboxybenzoyl)quinoline-2-carboxaldehyde (CBQCA).

The reactions between an aromatic dialdehyde and a primary amine or hydrazine have been reported to be used in methods of detecting alkyl primary amine (e.g., amino acids), hydrazine, or alkyl primary hydrazine (e.g., monomethylhydrazine and 1,1-dimethylhydrazine). See Collins et al., *Analyst*, 1994, 119, 1907-1913; U.S. Pat. Nos. 5,719,061; and 4,758,520. However, reactions between an aromatic dialdehyde and a non-alkyl amine, especially an electron deficient heteroaryl amine, were much less explored. Moreover, the reported reactions between an aromatic dialdehyde and a primary amine or hydrazine were conducted in solution. The effect of pursuing the reactions on solid supports was not reported.

There remains unmet needs to apply the reactions between an aromatic dialdehyde and a primary amine or hydrazine to a solid support material and to develop fast and high yield reaction conditions for more electron deficient amines. These new reaction conditions could find wide application in, e.g., step-wise quality control of bead manufacturing and DNA sequencing.

SUMMARY

Provided herein are processes for preparing fluorescent 1-cyano-2-substituted isoindole compounds or N-substituted phthalazinium compounds, comprising reacting an aromatic dialdehyde or aromatic aldehyde-ketone compound with a material that contains primary amino or hydrazine groups, and analytical methods involving the processes thereof.

In one embodiment, provided herein is a process for preparing a compound of Formula (I):

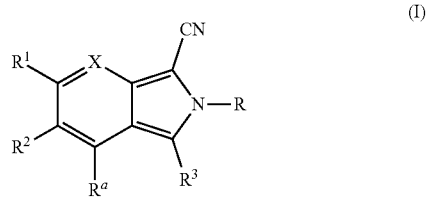

comprising reacting a compound of Formula (III):

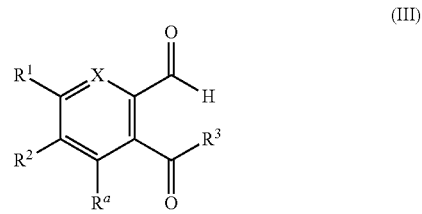

with a compound of R—$NH_2$ in the presence of a cyanide ion, wherein X, R, $R^1$, $R^2$, $R^3$, and $R^a$ are defined herein or elsewhere.

In one embodiment, provided herein is a method for assaying a compound of R—$NH_2$, comprising (i) reacting a sample containing the compound with a compound of Formula (III) in the presence of a cyanide ion to form a compound of Formula (I), and (ii) detecting and measuring the fluorescence of the compound of Formula (I).

In one embodiment, provided herein is a process for preparing a compound of Formula (II):

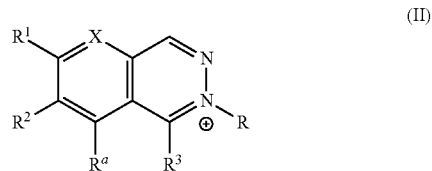

comprising reacting a compound of Formula (III):

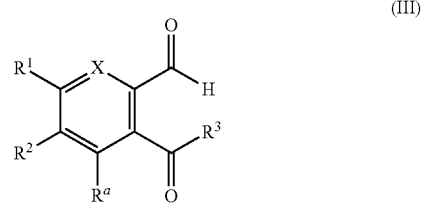

with a compound of R—$NHNH_2$, wherein X, R, $R^1$, $R^2$, $R^3$, and $R^a$ are defined herein or elsewhere.

In one embodiment, provided herein is a method for assaying a compound of R—$NHNH_2$, comprising (i) reacting a sample containing the compound with a compound of Formula (III) to form a compound of Formula (II), (ii)

optionally adjusting the pH to a suitable value, and (iii) detecting and measuring the fluorescence of the compound of Formula (II).

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

DETAILED DESCRIPTION

Definitions

Figure 1:
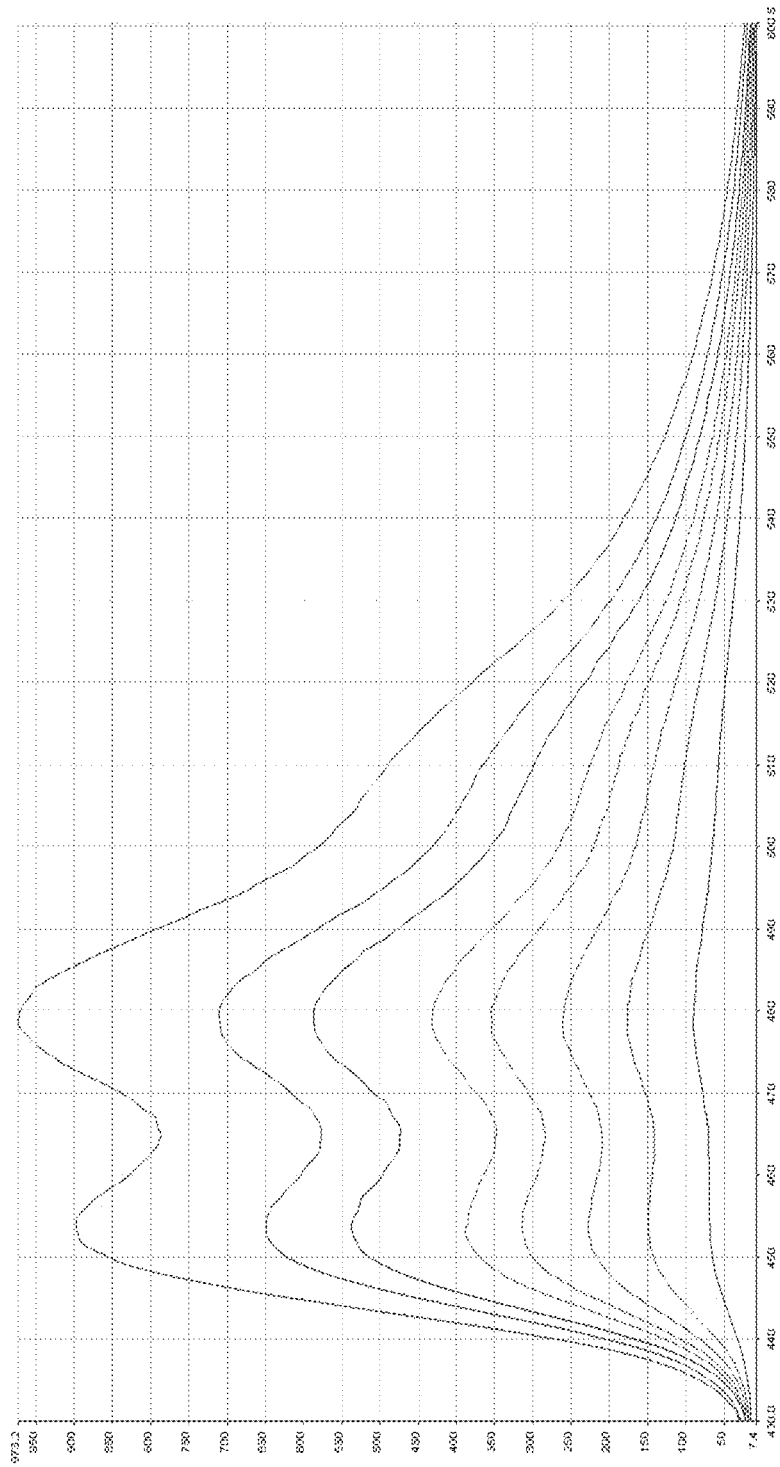
FIG. 1 shows a typical fluorescence emission spectrum of a product of Formula (I).

To facilitate understanding of the disclosure set forth herein, a number of terms are defined below. Generally, the nomenclature used herein and the laboratory procedures in organic chemistry described herein are those well known and commonly employed in the art. Unless defined otherwise, all technical and scientific terms used herein generally have the same meaning as commonly understood by one of ordinary skill in the art to which this disclosure belongs.

As used herein and unless otherwise indicated, the term "process(es)" provided herein refers to the methods described herein which are useful for preparing, analyzing, or using a compound provided herein. Modifications to the methods described herein (e.g., starting materials, reagents, protecting groups, solvents, temperatures, reaction times, purification) are also encompassed by the present disclosure.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive groups or the like can be added individually, simultaneously or separately and can be added in any order that achieves a desired result. They can be added in the presence or absence of a heating or cooling apparatus and can optionally be added under an inert atmosphere.

As used herein, and unless otherwise indicated, a reaction that is "substantially complete" or is driven to "substantial completion" means that the reaction contains more than about 50% by percent yield, in one embodiment more than about 60% by percent yield, in one embodiment more than about 70% by percent yield, in one embodiment more than about 80% by percent yield, in one embodiment more than about 90% by percent yield, in another embodiment more than about 95% by percent yield, and in another embodiment more than about 97% by percent yield of the desired product.

As used herein, and unless otherwise indicated, the term "salt" includes, but is not limited to, salts of acidic or basic groups that may be present in the compounds described herein. Compounds that are basic in nature are capable of forming a wide variety of salts with various inorganic and organic acids. The acids that may be used to prepare salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycolylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate/triphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise specified, the term "alkyl" refers to a linear or branched saturated hydrocarbon radical. The term "alkyl" also encompasses both linear and branched alkyl, unless otherwise specified. In certain embodiments, the alkyl is a linear saturated hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated hydrocarbon radical of 1 to 6 carbon atoms or a branched saturated hydrocarbon radical of 3 to 6 carbon atoms. The alkyl can be unsubstituted or substituted with one or more substituents. As used herein, the alkyl can be either a monovalent radical, or a multivalent radical (e.g., an alkylene) when it is described to be attached to more than one groups or moieties.

As used herein, and unless otherwise specified, the term "alkenyl" refers to a linear or branched hydrocarbon radical, which contains one or more, in one embodiment, one to five, carbon-carbon double bonds. The term "alkenyl" also embraces radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated hydrocarbon radical of 2 to 6 carbon atoms or a branched unsaturated hydrocarbon radical of 3 to 6 carbon atoms. In certain embodiments, the alkenyl is a linear hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. The alkenyl can be unsubstituted or substituted with one or more substituents. As used herein, the alkenyl can be either a monovalent radical, or a multivalent radical (e.g., an alkenylene) when it is described to be attached to more than one groups or moieties.

As used herein, and unless otherwise specified, the term "alkynyl" refers to a linear or branched hydrocarbon radical, which contains one or more, in one embodiment, one to five, carbon-carbon triple bonds. The term "alkynyl" also encompasses both linear and branched alkynyl, unless otherwise specified. In certain embodiments, the alkynyl is a linear hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated hydrocarbon radical of 2 to 6 carbon atoms or a branched unsaturated hydrocarbon radical of 3 to 6 carbon atoms. The alkynyl can be unsubstituted or substituted with one or more substituents. As used herein, the alkynyl can be either a monovalent radical, or a multivalent radical (e.g., an alkynylene) when it is described to be attached to more than one groups or moieties.

As used herein, and unless otherwise specified, the term "cycloalkyl" refers to a cyclic saturated or partially saturated hydrocarbon radical. The term "cycloalkyl" also encompasses fused cycloalkyl, bridged cycloalkyl, and spiro cycloalkyl. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, cycloheptadienyl, cycloheptatrienyl, decalinyl, and adamantyl. The cycloalkyl can be unsubstituted or substituted with one or more substituents. As used herein, the cycloalkyl can be either a monovalent radical, or a multivalent radical (e.g., a cycloalkylene) when it is described to be attached to more than one groups or moieties.

As used herein, and unless otherwise specified, the term "aryl" refers to a monocyclic aromatic group and/or multicyclic aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. The term "aryl" also refers to bicyclic, tricyclic, or other multicyclic hydrocarbon rings, where at least one of the rings is aromatic and the others of which may be saturated, partially unsaturated, or aromatic, for example, dihydronaphthyl, indenyl, indanyl, or tetrahydronaphthyl (tetralinyl). The aryl can be unsubstituted or substituted with one or more substituents. As used herein, the alkyl can be either a monovalent radical, or a multivalent radical (e.g., an arylene) when it is described to be attached to more than one groups or moieties.

As used herein, and unless otherwise specified, the term "heteroalkyl" refers to an alkyl radical that has one or more skeletal chain atoms selected from an atom other than carbon, e.g., oxygen, nitrogen, sulfur, and phosphorus, or combinations thereof. A numerical range can be given to refer to the chain length in total. For example, a —$CH_2OCH_2CH_3$ radical is referred to as a "C4" heteroalkyl. Connection to the parent molecular structure can be through either a heteroatom or a carbon in the heteroalkyl chain. One or more heteroatom(s) in the heteroalkyl radical can be optionally oxidized. One or more nitrogen atoms, if present, can also be optionally quaternized. The heteroalkyl can be unsubstituted or substituted with one or more substituents. As used herein, the heteroalkyl can be either a monovalent radical, or a multivalent radical (e.g., a heteroalkylene) when it is described to be attached to more than one groups or moieties.

As used herein, and unless otherwise specified, the term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. The term "heteroaryl" also refers to bicyclic, tricyclic, or other multicyclic rings, where at least one of the rings is aromatic and the others of which may be saturated, partially unsaturated, or aromatic, wherein at least one aromatic ring contains one or more heteroatoms independently selected from O, S, and N. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. The heteroaryl can be unsubstituted or substituted with one or more substituents. As used herein, the heteroaryl can be either a monovalent radical, or a multivalent radical (e.g., a heteroarylene) when it is described to be attached to more than one groups or moieties.

As used herein, and unless otherwise specified, the term "heterocyclyl" (or "heterocyclic") refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. The term "heterocyclyl" also encompasses fused heterocyclyl, bridged heterocyclyl, and spiro heterocyclyl. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the nitrogen or sulfur ring atoms may be optionally oxidized, and the nitrogen ring atoms may be optionally quaternized. The term "heterocyclyl" also refers to bicyclic, tricyclic, or other multicyclic rings, where at least one of the rings is non-aromatic and the others of which may be saturated, partially unsaturated, or aromatic, wherein at least one non-aromatic ring contains one or more heteroatoms independently selected from O, S, and N. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. The heterocyclyl or heterocyclic group can be unsubstituted or substituted with one or more substituents. As used herein, the heterocyclyl can be either a monovalent radical, or a multivalent radical (e.g., a heterocyclylene) when it is described to be attached to more than one groups or moieties.

As used herein, and unless otherwise specified, the term "halogen", "halide" or "halo" refers to fluorine, chlorine, bromine, and/or iodine.

As used herein, and unless otherwise specified, the term "alkoxy" refers to —O-(alkyl), wherein alkyl is defined above.

As used herein, and unless otherwise specified, the term "aryloxy" refers to —O-(aryl), wherein aryl is defined above.

As used herein, and unless otherwise specified, the term "cycloalkoxy" refers to —O-(cycloalkyl), wherein cycloalkyl is defined above.

As used herein, and unless otherwise specified, the term "heterocyclyloxy" refers to —O-(heterocyclyl), wherein heterocyclyl is defined above.

As used herein, and unless otherwise specified, the term "heteroaryloxy" refers to —O-(heteroaryl), wherein heteroaryl is defined above.

As used herein, and unless otherwise specified, the term "carboxyl" and "carboxy" refers to —COOH.

As used herein, and unless otherwise specified, the term "alkoxycarbonyl" refers to —C(=O)O-(alkyl), wherein alkyl is defined above. Examples of such alkoxycarbonyl groups include, but are not limited to, —C(=O)O—CH$_3$, —C(=O)O—CH$_2$CH$_3$, —C(=O)O—(CH$_2$)$_2$CH$_3$, —C(=O)O—(CH$_2$)$_3$CH$_3$, —C(=O)O—(CH$_2$)$_4$CH$_3$, —C(=O)O—(CH$_2$)$_5$CH$_3$, and the like.

As used herein, and unless otherwise specified, the term "acyl" refers to —C(O)—R$^t$, wherein R$^t$ can be, but is not limited to, hydrogen, alkyl, heteroalkyl, alkenyl, alkynyl, aryl, cycloalkyl, heteroaryl, heterocyclyl, each of which is defined above. In certain embodiments, R$^t$ may be unsubstituted or substituted with one or more substituents.

As used herein, and unless otherwise specified, the term "acyloxy" refers to —O—C(O)—R$^t$, wherein R$^t$ can be, but is not limited to, hydrogen, alkyl, heteroalkyl, alkenyl, alkynyl, aryl, cycloalkyl, heteroaryl, heterocyclyl, each of which is defined above. In certain embodiments, R$^t$ may be unsubstituted or substituted with one or more substituents.

As used herein, and unless otherwise specified, the term "amino" refers to —N(R$^o$)(R$^o$), wherein each R$^o$ independently can be, but is not limited to, hydrogen, alkyl, heteroalkyl, alkenyl, alkynyl, aryl, cycloalkyl, heteroaryl, heterocyclyl, each of which is defined above. When a —N(R$^o$)(R$^o$) group has two R$^o$ other than hydrogen, they can be combined with the nitrogen atom to form a ring. In one embodiment, the ring is a 3-, 4-, 5-, 6-, 7-, or 8-membered ring. In one embodiment, one or more ring atoms are heteroatoms independently selected from O, S, or N. As used herein, and unless otherwise specified, the term "primary amino" refers to —NH$_2$. The term "amino" also includes N-oxide-N$^+$(R$^o$)(R$^o$)O$^-$. In certain embodiments, each R$^o$ or the ring formed by —N(R$^o$)(R$^o$) independently may be unsubstituted or substituted with one or more substituents.

As used herein, and unless otherwise specified, the term "hydrazine" or "hydrazino" refers to —N(R$^o$)N(R$^o$)(R$^o$), wherein each R$^o$ independently can be, but is not limited to, hydrogen, alkyl, heteroalkyl, alkenyl, alkynyl, aryl, cycloalkyl, heteroaryl, heterocyclyl, each of which is defined above. When a —N(R$^o$)N(R$^o$)(R$^o$) group has two R$^o$ other than hydrogen, they can be combined with the nitrogen atom(s) to form a ring. In one embodiment, the ring is a 3-, 4-, 5-, 6-, 7-, or 8-membered ring. In one embodiment, one or more ring atoms are heteroatoms independently selected from O, S, or N. As used herein, and unless otherwise specified, the term "primary hydrazino" refers to —NHNH$_2$. In certain embodiments, each R$^o$ or the ring formed by —N(R$^o$)(R$^o$) independently may be unsubstituted or substituted with one or more substituents.

As used herein, and unless otherwise specified, the term "amide" or "amido" refers to —C(O)N(R$^o$)$_2$ or —NR$^o$C(O)R$^o$, wherein each R$^o$ independently can be, but is not limited to, hydrogen, alkyl, heteroalkyl, alkenyl, alkynyl, aryl, cycloalkyl, heteroaryl, heterocyclyl, each of which is defined above. When a —C(O)N(R$^o$)$_2$ group has two R$^o$ other than hydrogen, they can be combined with the nitrogen atom to form a ring. In one embodiment, the ring is a 3-, 4-, 5-, 6-, 7-, or 8-membered ring. In one embodiment, one or more ring atoms are heteroatoms independently selected from O, S, or N. In certain embodiments, each R$^o$ or the ring formed by —N(R$^o$)(R$^o$) independently may be unsubstituted or substituted with one or more substituents.

As used herein, and unless otherwise specified, the term "sulfanyl", "sulfide", or "thio" refers to —S—R$^t$, wherein R$^t$ can be, but is not limited to, alkyl, heteroalkyl, alkenyl, alkynyl, aryl, cycloalkyl, heteroaryl, heterocyclyl, each of which is defined above. In certain embodiments, R$^t$ may be unsubstituted or substituted with one or more substituents.

As used herein, and unless otherwise specified, the term "sulfoxide" refers to —S(O)—R$^t$, wherein R$^t$ can be, but is not limited to, alkyl, heteroalkyl, alkenyl, alkynyl, aryl, cycloalkyl, heteroaryl, heterocyclyl, each of which is defined above. In certain embodiments, R$^t$ may be unsubstituted or substituted with one or more substituents.

As used herein, and unless otherwise specified, the term "sulfonyl" or "sulfone" refers to —S(O)$_2$—R$^t$, wherein R$^t$ can be, but is not limited to, alkyl, heteroalkyl, alkenyl, alkynyl, aryl, cycloalkyl, heteroaryl, heterocyclyl, each of which is defined above. In certain embodiments, R$^o$ may be unsubstituted or substituted with one or more substituents.

As used herein, and unless otherwise specified, the term "sulfonamido" or "sulfonamide" refers to) —S(=O)$_2$—N(R$^o$)$_2$ or —N(R$^o$)—S(=O)$_2$—R$^o$, wherein each R$^o$ independently can be, but is not limited to, hydrogen, alkyl, heteroalkyl, alkenyl, alkynyl, aryl, cycloalkyl, heteroaryl, heterocyclyl, each of which is defined above. When a —S(=O)$_2$—N(R$^o$)$_2$ group has two R$^o$ other than hydrogen, they can be combined with the nitrogen atom to form a ring. In one embodiment, the ring is a 3-, 4-, 5-, 6-, 7-, or 8-membered ring. In one embodiment, one or more ring atoms are heteroatoms independently selected from O, S, or N. In certain embodiments, each R$^o$ or the ring formed by —N(R$^o$)(R$^o$) independently may be unsubstituted or substituted with one or more substituents.

When the groups described herein are said to be "substituted," they may be substituted with any appropriate substituent or substituents. Illustrative examples of substituents include, but are not limited to, those found in the exemplary compounds and embodiments described herein, as well as halogen (chloro, iodo, bromo, or fluoro); alkyl; alkenyl; alkynyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aryloxyamine, aralkoxyamine; N-oxide; hydrazine; hydrazide; hydrazone; azide; isocyanate; isothiocyanate; cyanate; thiocyanate; oxo (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, and unless otherwise specified, the term "isomer" refers to different compounds that have the same molecular formula. "Stereoisomers" are isomers that differ only in the way the atoms are arranged in space. "Atropisomers" are stereoisomers from hindered rotation about single bonds. "Enantiomers" are a pair of stereoisomers that are non-superimposable mirror images of each other. A mixture of a pair of enantiomers in any proportion can be known as a "racemic" mixture. "Diastereoisomers" are stereoisomers that have at least two asymmetric atoms, but which are not mirror-images of each other. The absolute stereochemistry can be specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. However, the sign of optical rotation, (+) and (−), is not related to the absolute configuration of the molecule, R and S. Certain of the compounds described herein contain one or more asymmetric centers and can thus give rise to enantiomers, diastereomers, and other stereoisomeric forms that can be defined, in terms of absolute stereochemistry at each asymmetric atom, as (R)— or (S)—. The present chemical entities, pharmaceutical compositions and methods are meant to include all such possible isomers, including racemic mixtures, optically substantially pure forms and intermediate mixtures. Optically active (R)— and (S)— isomers can be prepared, for example, using chiral synthons or chiral reagents, or resolved using conventional techniques.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, and unless otherwise specified, the term "solid support" or other grammatical equivalents refers to any material that contains and/or can be modified to contain one or more sites (e.g., discrete individual sites, pre-defined sites, random sites, etc.) appropriate for the attachment or association of compositions (e.g., an organic molecule or moiety) disclosed herein. Exemplary solid supports include, but are not limited to, glass and modified or functionalized glass, plastics (including acrylics, polystyrene and copolymers of styrene and other materials, polypropylene, polyethylene, polybutylene, polyurethanes, TEFLON™ (polytetrafluoroethylene), etc.), polysaccharides, nylon or nitrocellulose, resins, silica or silica-based materials including silicon and modified silicon, carbon, metals, inorganic glasses, optical fiber bundles, nanoparticles (e.g. inorganic nanoparticles (NPs) of cerium oxide (CeO$_2$), iron oxide (Fe$_3$O$_4$) and titanium oxide (TiO$_2$); or organic and bioorganic nanoparticles of lipids, nanocages, dendrimers, supermolecular nanoparticles, self-assembly nanoparticles), and a variety of other polymers. In particular embodiments, the solid supports allow optical detection and do not themselves appreciably fluoresce. The compositions (e.g., an organic molecule or moiety) can attach to the macromolecule directly or via a linker. As used herein, and unless otherwise specified, the term "linker" refers to the molecular fragment or moiety that joins the solid support and the compositions.

A solid support can be flat (planar), although as will be appreciated by those in the art, other configurations of solid supports may be used as well; for example, three dimensional configurations can be used, for example by embedding beads in a porous block of plastic that allows sample access to the beads and using a confocal microscope for detection. Similarly, the beads may be placed on the inside surface of a tube, for flow-through sample analysis to minimize sample volume. In some aspects solid supports include optical fiber bundles and flat planar solid supports such as glass, polystyrene and other plastics and acrylics. A bead includes a small discrete particle, the composition of which will depend on the class of probe used and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as SEPHAROSE™ (cross-linked beaded-form of agarose), cellulose, nylon, cross-linked micelles and TEFLON™ (polytetrafluoroethylene) may all be used. See, e.g., "Microsphere Detection Guide" from Bangs Laboratories, Fishers IN.

Unless otherwise indicated, the compounds provided herein, including intermediates useful for the preparation of the compounds provided herein, which contain reactive functional groups (such as, without limitation, carboxy, hydroxy, and amino moieties) also include protected derivatives thereof "Protected derivatives" are those compounds in which a reactive site or sites are blocked with one or more protecting groups (also known as blocking groups). Suitable protecting groups are well known to those of ordinary skill in the art. The choice and use of protecting groups and the reaction conditions to install and remove protecting groups are described in T W Greene, *Protective Groups in Organic Synthesis* (Third Ed., Wiley, New York, 1999), which is incorporated herein by reference in its entirety.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Processes and Assaying Methods

In one embodiment, provided herein is a process for preparing a compound of Formula (I):

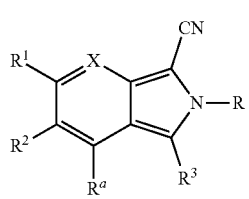

(I)

comprising reacting a compound of Formula (III):

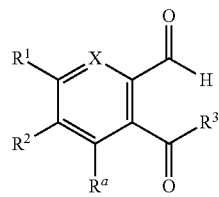

(III)

with a compound of R—NH$_2$ in the presence of a cyanide ion,
wherein:
X is CR$^a$ or N,
R$^1$ and R$^2$ are R$^a$; or R$^1$ and R$^2$ together with the carbon atoms they are attached to form a monocyclic or multicyclic fused aryl or heteroaryl ring, which is optionally substituted with one or more R$^{a1}$;
R$^3$ is hydrogen, alkyl, cycloalkyl, heterocyclyl, aryl, or heteroaryl; each of which is optionally substituted with one or more R$^b$;
R is a moiety, which is attached to a solid support directly or via a linker;

each instance of R$^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$;
each instance of R$^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$; and
each instance of R$^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, X is CR$^a$. In one embodiment, provided herein is a process for preparing a compound of Formula (I-a):

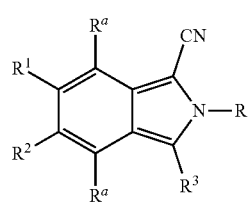

(I-a)

comprising reacting a compound of Formula (III-a):

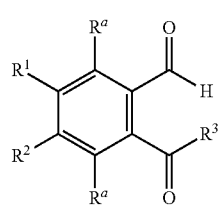

(III-a)

with a compound of R—NH$_2$ in the presence of a cyanide ion,
wherein:
R$^1$ and R$^2$ are R$^a$; or R$^1$ and R$^2$ together with the carbon atoms they are attached to form a monocyclic or multicyclic fused aryl or heteroaryl ring, which is optionally substituted with one or more R$^{a1}$;
R$^3$ is hydrogen, alkyl, cycloalkyl, heterocyclyl, aryl, or heteroaryl; each of which is optionally substituted with one or more R$^b$;
R is a moiety, which is attached to a solid support directly or via a linker;
each instance of R$^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;

each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, X is N. In one embodiment, provided herein is a process for preparing a compound of Formula (I-b):

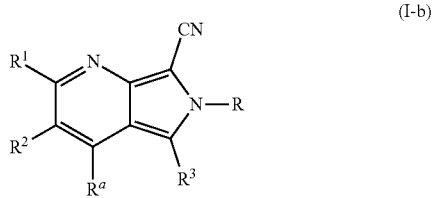

(I-b)

comprising reacting a compound of Formula (III-b):

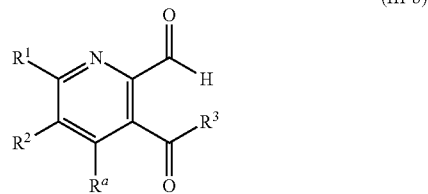

(III-b)

with a compound of R—$NH_2$ in the presence of a cyanide ion,
wherein:
$R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;

$R^3$ is hydrogen, alkyl, cycloalkyl, heterocyclyl, aryl, or heteroaryl; each of which is optionally substituted with one or more $R^b$;

R is a moiety, which is attached to a solid support directly or via a linker;

each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;

each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, R is optionally substituted alkyl, cycloalkyl, heterocyclyl, aryl, or heteroaryl, which is attached to a solid support directly or via a linker. In one embodiment, R is optionally substituted alkyl, aryl, or heteroaryl, which is attached to a solid support directly or via a linker. In some embodiments, R is optionally substituted with one or more substituents independently selected from the group consisting of alkyl, halo, chloro, hydroxyl, amino, hydrazino, alkoxy, cyano, amido, carboxyl, —NHC(O)NHNH$_2$, —NHC(O)NH—N═C(H)-oligonucleotide, and —NH—N═C(H)-oligonucleotide. In some embodiments, R is optionally substituted with or more substituents independently selected from the group consisting of chloro, amino, hydrazine, and —NH—N═C(H)-oligonucleotide. In such embodiments, the oligonucleotide portion of —NH—N═C(H)-oligonucleotide or —NHC(O)NH—N═C(H)-oligonucleotide is the condensation product of an oligonucleotide with an aldehyde substituent and a hydrazine moiety or a —NHC(O)NHNH$_2$ moiety, respectively.

In one embodiment, R is optionally substituted alkyl, which is attached to a solid support directly or via a linker. In further embodiments, R is optionally substituted $C_{2-10}$alkyl or $C_{2-6}$alkyl or $C_{3-5}$alkyl or propyl. In further embodiments, R is $C_{2-10}$alkyl or $C_{2-6}$alkyl or $C_{3-5}$alkyl or propyl.

In one embodiment, R—$NH_2$ is an optionally substituted amino acid, which is attached to a solid support directly or via a linker. In one embodiment, R—$NH_2$ is optionally substituted peptide, which is attached to a solid support directly or via a linker.

In one embodiment, R is optionally substituted aryl, which is attached to a solid support directly or via a linker. In one embodiment, R is optionally substituted phenyl, which is attached to a solid support directly or via a linker.

In one embodiment, R is optionally substituted 5- or 6-membered monocyclic heteroaryl, which is attached to a solid support directly or via a linker. In one embodiment, R is optionally substituted pyrimidyl, which is attached to a solid support directly or via a linker. In one embodiment, R is optionally substituted triazinyl, which is attached to a solid support directly or via a linker. In some embodiments, R is triazinyl, optionally substituted with one or more substituents as described above. In some embodiments, R is triazinyl, optionally substituted with one or more substituents selected from the group consisting of chloro, hydrazino, —NHC(O)NHNH$_2$, —NHC(O)NH—N═C(H)-oligonucleotide, and —NH—N═C(H)-oligonucleotide.

In one embodiment, R is optionally substituted 9- or 10-membered bicyclic fused heteroaryl, which is attached to a solid support directly or via a linker. In one embodiment, R is optionally substituted purinyl, which is attached to a solid support directly or via a linker.

In one embodiment, R—$NH_2$ is optionally substituted nucleobase, which is attached to a solid support directly or via a linker. In one embodiment, the nucleobase is cytosine, guanine, adenine, thymine, 7-methylguanine, 7-methylguanosine, 5-methylcytosine, 5-hydroxymethylcytosine, or 5-methylcytidine, which is attached to a solid support directly or via a linker. In one embodiment, the nucleobase is attached to a sugar moiety, which is further attached to a solid support directly or via a linker. In one embodiment, the sugar moiety is a ribose or 2-deoxyribose.

In one embodiment, R—NH$_2$ is optionally substituted nucleoside, which is attached to a solid support directly or via a linker. In one embodiment, R—NH$_2$ is optionally substituted nucleotide, which is attached to a solid support directly or via a linker.

In one embodiment, R is —NH—, -alkyl-NH—, —NHC(O)NH—, or -alkyl-NHC(O)NH—. In other embodiments, R is —NHC(O)NH— or -alkyl-NHC(O)NH—. In other embodiments, R—NH$_2$ is —NH—NH$_2$ or —NHC(O)NHNH$_2$. In other embodiments, R—NH$_2$ is optionally substituted alkyl-NH—C(O)NHNH$_2$, which is attached to a solid support directly or via a linker. In further embodiments, R—NH$_2$ is C$_{3-6}$alkyl-NH—C(O)NHNH$_2$, or is propyl-NH—C(O)NHNH$_2$.

In one embodiment, R is an electron deficient group or electron withdrawing group, which is attached to a solid support directly or via a linker. In one embodiment, the —NH$_2$ group in R—NH$_2$ has a pKa of from about 7 to about 10, from about 7.5 to about 10, from about 8 to about 10, from about 8.5 to about 10, or from about 9 to about 10. In one embodiment, the —NH$_2$ in R—NH$_2$ group has a pKa of from about 7.4 to about 10.

In one embodiment, the —NH$_2$ group in R—NH$_2$ has a pKa of from about 7 to about 8, from about 8 to about 9, or from about 9 to about 10.

In one embodiment, the solid support is one or more of glass and modified or functionalized glass, plastics (including acrylics, polystyrene and copolymers of styrene and other materials, polypropylene, polyethylene, polybutylene, polyurethanes, TEFLON™ (polytetrafluoroethylene), etc.), polysaccharides, nylon or nitrocellulose, resins, silica or silica-based materials including silicon and modified silicon, carbon, metals, inorganic glasses, optical fiber bundles, and a variety of other polymers. In one embodiment, the solid support is flat. In one embodiment, the solid support is a bead (e.g., Spherical silica beads, Inorganic nanoparticles (NPs) of iron oxide (Fe$_3$O$_4$) and metal particles (e.g., gold and silver), magnetic nanoparticles cadmium based dots, and cadmium free dots). Particularly useful solid supports include silica beads and bead arrays such as those described in U.S. Pat. Nos. 6,266,459; 6,355,431; 6,770,441; 6,859,570; 6,210,891; 6,258,568; 6,274,320; U.S. Patent Application Publication Nos. 2009/0026082 A1; 2009/0127589 A1; 2010/0137143 A1; 2010/0282617 A1; or PCT Publication No. WO 00/63437; the entirety of each of which is incorporated herein by reference; or those commercialized in BeadArray™ platforms marketed by Illumina, Inc. (San Diego, CA). Other useful solid supports are those that are used in flow cells. Exemplary flow cells include, but are not limited to, those used in a nucleic acid sequencing apparatus such as flow cells for the NovaSeq®, Genome Analyzer®, MiSeq®, NextSeq® or HiSeq® platforms commercialized by Illumina, Inc. (San Diego, CA); or for the SOLiD™ or Ion Torrent™ sequencing platform commercialized by Life Technologies (Carlsbad, CA). Exemplary flow cells, their compositions and methods for their manufacture and use are also described, for example, in PCT Publication No. WO 2014/142841 A1; U.S. Patent Application Publication No. 2010/0111768 A1; and U.S. Pat. No. 8,951,781; the entirety of each of which is incorporated herein by reference.

In one embodiment, the moiety of R is attached to the solid support. The moiety of R can be an organic moiety (e.g., carbon atom or carbon-containing moiety or amine or oxy derivative) or an inorganic moiety (e.g., a silane). In some embodiments, R can be a gel or a linker that is attached to a gel. The gel can, in turn, be attached to the solid support, for example, via covalent bonding or non-covalent association. Useful gels include, but are not limited to hydrogels such as acrylamide, methacrylamide, hydroxyethyl methacrylate, N-vinyl pyrolidinone or derivatives thereof. In some embodiments, the gel can include two or more different species of compound that form a co-polymer. For example, two or more different species of acrylamide, methacrylamide, hydroxyethyl methacrylate, N-vinyl pyrolidinone or derivatives thereof can function as co-monomers that polymerize to form a copolymer hydrogel. Useful hydrogels include, but are not limited to, silane-free acrylamide (SFA) polymer (see, e.g., U.S. Patent Application Publication No. 2011/0059865 A1, the entirety of which is incorporated herein by reference), poly(N-(5-azidoacetamidylpentyl)acrylamide-co-acrylamide) (PAZAM) (see, e.g., U.S. Pat. No. 9,012,022, the entirety of which is incorporated herein by reference), polyacrylamide polymers formed from acrylamide and an acrylic acid or an acrylic acid containing a vinyl group as described, for example, in PCT Publication No. WO 00/31148, the entirety of which is incorporated herein by reference; polyacrylamide polymers formed from monomers that form [2+2] photo-cycloaddition reactions, for example, as described in PCT Publication Nos. WO 01/01143 or WO 03/014392, the entirety of each of which is incorporated herein by reference; or polyacrylamide copolymers as described, for example, in U.S. Pat. No. 6,465,178, PCT Publication Nos. WO 01/62982 and WO 00/53812, the entirety of each of which is incorporated herein by reference.

In one embodiment, the moiety of R is attached to the solid support via a linker. In one embodiment, the linker comprises one or more linker units selected from the group consisting of mono-hydrazinyl-1,3,5-triazine, di-hydrazinyl-1,3,5-triazine or hydrazinecarboxamide. In one embodiment, the linker comprises one linker unit. In one embodiment, the linker comprises two linker units. In one embodiment, the linker comprises three or more linker units. The multiple linker units in a linker can be identical or different.

In one embodiment, the compound of R—NH$_2$ is (3-aminopropyl)-silane.

In one embodiment, the compound of R—NH$_2$ is attached to a solid support, and together with the solid support comprises a compound of one or the following structures:

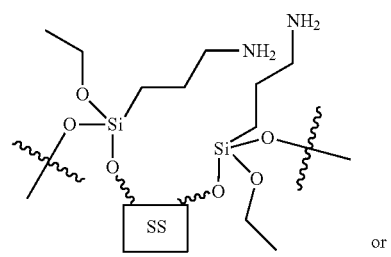

or

-continued

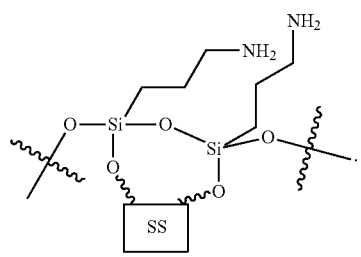

[SS] in the structures indicates a solid support. The wave lines in the structures indicate open linkage to adjacent molecules or H or alkyl groups. In other embodiments, R—NH₂ is attached to a solid support, and together with the solid support and optional linker comprises: [SS]-OSi(OZ)₂-alkyl-NH₂, wherein each Z is alkyl, H, or a silicon atom of an adjacent solid support-bound group. In some embodiments, each alkyl is independently C$_{2-6}$alkyl.

In other embodiments, R—NH₂ is attached to a solid support, and together with the solid support comprises a compound of one or the following structures, or tautomers thereof:

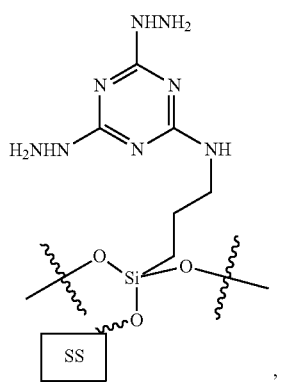

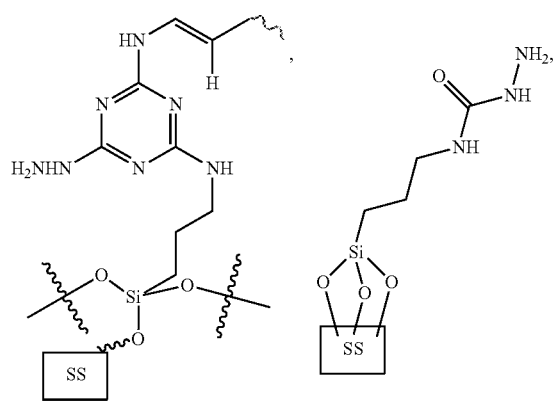

-continued

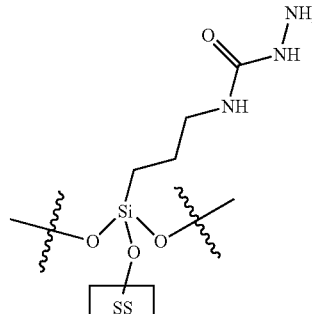

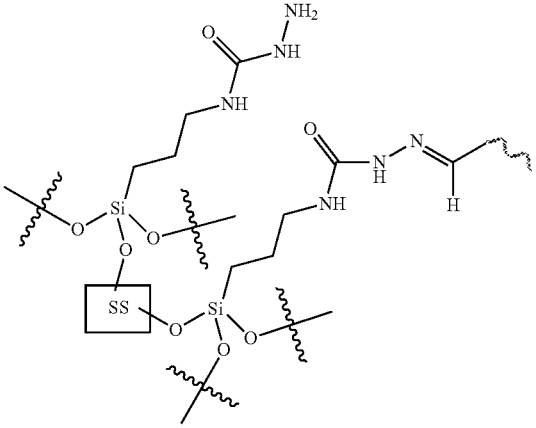

wherein the strand moiety is a nucleic acid molecule, such as DNA. The wave lines in the structures indicate open linkage to adjacent molecules or H or alkyl groups. [SS] in the structures indicates a solid support. In some embodiments, R—NHNH₂ is attached to a solid support, and together with the solid support and optional linker comprises: [SS]-OSi(OZ)₂-alkyl-NHC(O)NHNH₂, wherein Z is alkyl, H, or a silicon atom of an adjacent solid support-bound group. In some embodiments, each alkyl is independently C$_{2-6}$alkyl.

In some embodiments, R—NH₂ is attached to a solid support via a linker. In some embodiments, a linker comprises one or more functional groups such as alkyl, heteroalkyl (e.g., polyethylene glycol), peptide, silanes, alkoxysilanes, or other suitable linker groups. In some embodiments, the linker is —OSi(OZ)₂— or —OSi(OZ)₂-alkyl-(NH)$_{0-1}$, where Z is as defined above. In other embodiments, the linker is —OSi(OZ)₂-propyl- or —OSi(OZ)₂-propyl-NH—.

In some embodiments, X is CR$^a$. In other embodiments, X is N.

In some embodiments, R$^1$ and R$^2$ are each R$^a$. In other embodiments, R$^1$ and R$^2$ together with the carbon atoms to which they are attached form a monocyclic or multicyclic aryl or heteroaryl ring, optionally substituted with one or more R$^{a1}$. In some embodiments, R$^1$ and R$^2$ together with the carbon atoms to which they are attached form an optionally substituted phenyl or naphthyl ring. In other embodiments, R$^1$ and R$^2$ together with the carbon atoms to which they are attached form an optionally substituted monocyclic heteroaryl ring.

In some embodiments, R$^3$ is hydrogen, alkyl, aryl, or heteroaryl. In other embodiments, R$^3$ is hydrogen.

In some embodiments, each instance of R$^a$ is independently hydrogen, halo, cyano, alkyl, hydroxyl, or alkoxy. In other embodiments, each instance of R$^a$ is hydrogen.

In some embodiments, each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, arloxy, heteroaryloxy, cyano, nitro, amino, amido, carboxyl, acyl, acyloxy, or alkoxycarbonyl. In other embodiments, each instance of $R^{a1}$ is independently halogen, alkyl, hydroxyl, alkoxy, cyano, amido, carboxyl, acyl, acyloxy, or alkoxycarbonyl. In still other embodiments, each instance of $R^{a1}$ is independently halogen, alkyl, hydroxyl, alkoxy, or cyano.

In some embodiments, each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, acyl, acyloxy, or alkoxycarbonyl. In other embodiments, each instance of $R^b$ is independently halogen, alkyl, hydroxyl, alkoxy, cyano, amido, carboxyl, acyl, acyloxy, or alkoxycarbonyl. In still other embodiments, each instance of $R^b$ is independently halogen, alkyl, hydroxyl, alkoxy, carboxy, or cyano.

In one embodiment, provided herein is a process for preparing a compound of Formula (I):

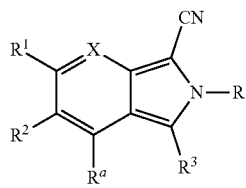

(I)

comprising reacting a compound of Formula (III):

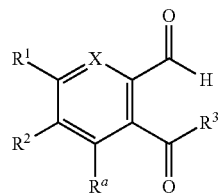

(III)

with a compound of R—NH$_2$ in the presence of a cyanide ion,
wherein:
X is $CR^a$ or N,
$R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;
$R^3$ is hydrogen, alkyl, cycloalkyl, heterocyclyl, aryl, or heteroaryl; each of which is optionally substituted with one or more $R^b$;
R is optionally substituted heteroaryl;
each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;
each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and
each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy;
provided that R is not 2-pyridyl or 3-pyridyl.

In one embodiment, X is $CR^a$. In one embodiment, provided herein is a process for preparing a compound of Formula (I-a):

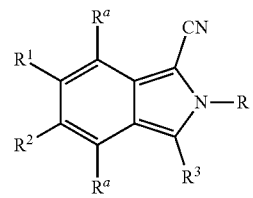

(I-a)

comprising reacting a compound of Formula (III-a):

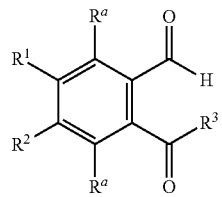

(III-a)

with a compound of R—NH$_2$ in the presence of a cyanide ion,
wherein:
$R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;
$R^3$ is hydrogen, alkyl, cycloalkyl, heterocyclyl, aryl, or heteroaryl; each of which is optionally substituted with one or more $R^b$;
R is optionally substituted heteroaryl;
each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;
each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy;

provided that R is not 2-pyridyl or 3-pyridyl.

In one embodiment, X is N. In one embodiment, provided herein is a process for preparing a compound of Formula (I-b):

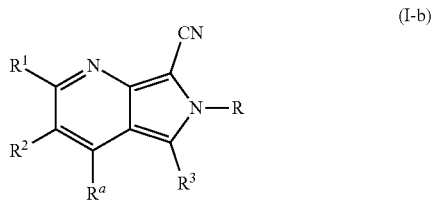

(I-b)

comprising reacting a compound of Formula (III-b):

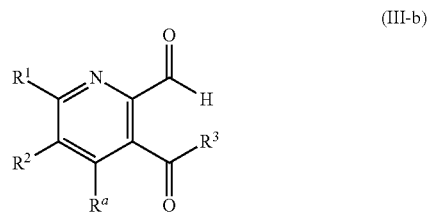

(III-b)

with a compound of R—NH$_2$ in the presence of a cyanide ion,
wherein:
    $R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;
    $R^3$ is hydrogen, alkyl, cycloalkyl, heterocyclyl, aryl, or heteroaryl; each of which is optionally substituted with one or more $R^b$;
    R is optionally substituted heteroaryl;
    each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;
    each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and
    each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy;

provided that R is not 2-pyridyl or 3-pyridyl.

In one embodiment, R is optionally substituted 5- or 6-membered monocyclic heteroaryl. In one embodiment, R is optionally substituted pyrimidyl. In one embodiment, R is optionally substituted triazinyl. In some embodiments, R is triazinyl, optionally substituted with one or more substituents as described above. In some embodiments, R is triazinyl, optionally substituted with one or more substituents selected from the group consisting of chloro, hydrazino, —NHC(O)NHNH$_2$, —NHC(O)NH—N═C(H)-oligonucleotide, and —NH—N═C(H)-oligonucleotide.

In one embodiment, R is optionally substituted 9- or 10-membered bicyclic fused heteroaryl. In one embodiment, R is optionally substituted purinyl.

In one embodiment, R—NH$_2$ is optionally substituted nucleobase. In one embodiment, the nucleobase is cytosine, guanine, adenine, thymine, 7-methylguanine, 7-methylguanosine, 5-methylcytosine, 5-hydroxymethylcytosine, or 5-methylcytidine. In one embodiment, the nucleobase is attached to a sugar moiety. In one embodiment, the sugar moiety is a ribose or 2-deoxyribose.

In one embodiment, R—NH$_2$ is optionally substituted nucleoside. In one embodiment, R—NH$_2$ is optionally substituted nucleotide.

In one embodiment, R is an electron deficient group or electron withdrawing group, which is attached to a solid support directly or via a linker. In one embodiment, the —NH$_2$ group in R—NH$_2$ has a pKa of from about 7 to about 10, from about 7.5 to about 10, from about 8 to about 10, from about 8.5 to about 10, or from about 9 to about 10. In one embodiment, the —NH$_2$ group in R—NH$_2$ has a pKa of from about 7.4 to about 10.

In one embodiment, the —NH$_2$ group of R—NH$_2$ in R—NH$_2$ has a pKa of from about 7 to about 8, from about 8 to about 9, or from about 9 to about 10.

In one embodiment, the cyanide ion for the preparation of the compound of Formula (I) is provided from a cyanide source. In one embodiment, the cyanide source is potassium cyanide. In another embodiment, the cyanide source is sodium cyanide.

In one embodiment, the reaction between the compound of Formula (III) and R—NH$_2$ occurs under a mildly basic condition. In one embodiment, the mildly basic condition has a pH of from about 7.5 to about 10.

In one embodiment, the reaction between the compound of Formula (III) and R—NH$_2$ occurs in a solvent. In one embodiment, the solvent comprises a buffer solution. In one embodiment, the solvent is a mixture of a water miscible solvent and a buffer solution. In one embodiment, the solvent is a mixture of an alcohol and a buffer solution. In one embodiment, the alcohol is methanol. In another embodiment, the alcohol is ethanol. In one embodiment, the buffer solution is a borate buffer solution. In another embodiment, the buffer solution is a phosphate buffer solution.

In one embodiment, the solvent is a mixture (e.g., about 1:1 mixture) of methanol and borate buffer (e.g., about pH 9.5). In one embodiment, the solvent is a mixture (e.g., about 1:1 mixture) of ethanol and borate buffer (e.g., about pH 9.5). In one embodiment, the solvent is a mixture (e.g., about 1:1 mixture) of methanol and phosphate buffer (e.g., about pH 7.5-8.5). In one embodiment, the solvent is a mixture (e.g., about 1:1 mixture) of ethanol and phosphate buffer (e.g., about pH 7.5-8.5).

In one embodiment, the reaction between the compound of Formula (III) and R—NH₂ achieves substantial completion from about 1 minute to about 6 hours. In one embodiment, the reaction between the compound of Formula (III) and R—NH₂ achieves at least 50%, at least 60%, at least 70%, at least 80%, at least 85%, at least 90%, at least 95%, at least 97.5%, at least 99%, at least 99.5%, or at least 99.9% yield within about 6 hours, about 4 hours, about 2 hours, about 1 hour, about 30 minutes, about 15 minutes, about 10 minutes, or about 5 minutes. In one embodiment, the reaction between the compound of Formula (III) and R—NH₂ achieves at least 70% yield within about 1 hour. In one embodiment, the reaction between the compound of Formula (III) and R—NH₂ achieves at least 90% yield within about 1 hour. In one embodiment, the reaction between the compound of Formula (III) and R—NH₂ achieves at least 70% yield within about 30 minutes. In one embodiment, the reaction between the compound of Formula (III) and R—NH₂ achieves at least 90% yield within about 30 minutes.

In one embodiment, provided herein is a process for preparing a compound of Formula (II):

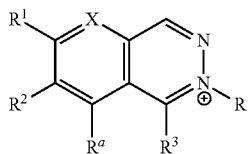

(II)

comprising reacting a compound of Formula (III):

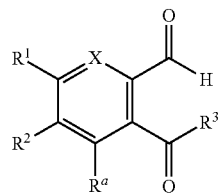

(III)

with a compound of R—NHNH₂,
wherein:
X is CR$^a$ or N,
R$^1$ and R$^2$ are R$^a$; or R$^1$ and R$^2$ together with the carbon atoms they are attached to form a monocyclic or multicyclic fused aryl or heteroaryl ring, which is optionally substituted with one or more R$^{a1}$;
R$^3$ is hydrogen, alkyl, cycloalkyl, heterocyclyl, aryl, or heteroaryl; each of which is optionally substituted with one or more R$^b$;
R is a moiety, which is attached to a solid support directly or via a linker;
each instance of R$^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$;
each instance of R$^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$; and
each instance of R$^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, X is CR$^a$. In one embodiment, provided herein is a process for preparing a compound of Formula (II-a):

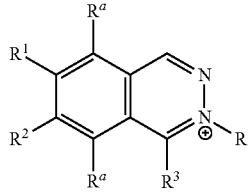

(II-a)

comprising reacting a compound of Formula (III-a):

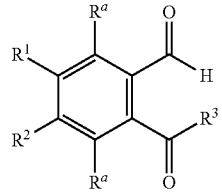

(III-a)

with a compound of R—NHNH₂,
wherein:
R$^1$ and R$^2$ are R$^a$; or R$^1$ and R$^2$ together with the carbon atoms they are attached to form a monocyclic or multicyclic fused aryl or heteroaryl ring, which is optionally substituted with one or more R$^{a1}$;
R$^3$ is hydrogen, alkyl, cycloalkyl, heterocyclyl, aryl, or heteroaryl; each of which is optionally substituted with one or more R$^b$;
R is a moiety, which is attached to a solid support directly or via a linker;
each instance of R$^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$;
each instance of R$^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$; and
each instance of R$^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, X is N. In one embodiment, provided herein is a process for preparing a compound of Formula (II-b):

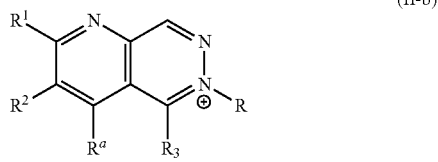

comprising reacting a compound of Formula (III-b):

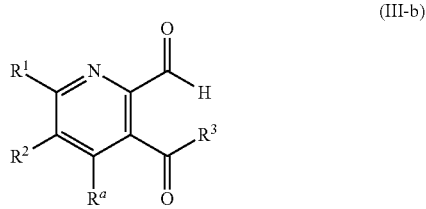

with a compound of R—NHNH$_2$,
wherein:
  $R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;
  $R^3$ is hydrogen, alkyl, cycloalkyl, heterocyclyl, aryl, or heteroaryl; each of which is optionally substituted with one or more $R^b$;
  R is a moiety, which is attached to a solid support directly or via a linker;
  each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;
  each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and
  each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, R is optionally substituted alkyl, cycloalkyl, heterocyclyl, aryl, or heteroaryl, which is attached to a solid support directly or via a linker. In one embodiment, R is optionally substituted alkyl, aryl, or heteroaryl, which is attached to a solid support directly or via a linker. In some embodiments, R is optionally substituted with one or more substituents independently selected from the group consisting of alkyl, halo, chloro, hydroxyl, amino, hydrazino, alkoxy, cyano, amido, carboxyl, —NHC(O)NHNH$_2$, —NHC(O)NH—N=C(H)-oligonucleotide, and —NH—N=C(H)-oligonucleotide. In some embodiments, R is optionally substituted with or more substituents independently selected from the group consisting of chloro, amino, hydrazine, and —NH—N=C(H)-oligonucleotide. In such embodiments, the oligonucleotide portion of —NH—N=C(H)-oligonucleotide or —NHC(O)NHN=C(H)-oligonucleotide is the condensation product of an oligonucleotide with an aldehyde substituent and a hydrazine moiety or —NHC(O)NHNH$_2$ moiety, respectively.

In one embodiment, R is optionally substituted alkyl, which is attached to a solid support directly or via a linker. In further embodiments, R is optionally substituted $C_{2-10}$alkyl or $C_{2-6}$alkyl or $C_{3-5}$alkyl or propyl. In further embodiments, R is $C_{2-10}$alkyl or $C_{2-6}$alkyl or $C_{3-5}$alkyl or propyl.

In one embodiment, R is optionally substituted aryl, which is attached to a solid support directly or via a linker. In one embodiment, R is optionally substituted phenyl, which is attached to a solid support directly or via a linker.

In one embodiment, R is optionally substituted 5- or 6-membered monocyclic heteroaryl, which is attached to a solid support directly or via a linker. In one embodiment, R is optionally substituted pyrimidyl, which is attached to a solid support directly or via a linker. In one embodiment, R is optionally substituted triazinyl, which is attached to a solid support directly or via a linker. In some embodiments, R is triazinyl, optionally substituted with one or more substituents as described above. In some embodiments, R is triazinyl, optionally substituted with one or more substituents selected from the group consisting of chloro, hydrazino, —NHC(O)NHNH$_2$, —NHC(O)NH—N=C(H)-oligonucleotide, and —NH—N=C(H)-oligonucleotide.

In one embodiment, R is optionally substituted 9- or 10-membered bicyclic fused heteroaryl, which is attached to a solid support directly or via a linker. In one embodiment, R is optionally substituted purinyl, which is attached to a solid support directly or via a linker.

In one embodiment, R is optionally substituted aminocarbonyl (NH—C=O), which is attached to a solid support directly or via a linker. In one embodiment, R is optionally substituted alkylaminocarbonyl (alkyl-NH—C=O), which is attached to a solid support directly or via a linker. In some embodiments, R is $C_{2-6}$alkyl-NHC(O)—. In other embodiments, R is propyl-NHC(O)—.

In one embodiment, the solid support is one or more of glass and modified or functionalized glass, plastics (including acrylics, polystyrene and copolymers of styrene and other materials, polypropylene, polyethylene, polybutylene, polyurethanes, TEFLON™ (polytetrafluoroethylene), etc.), polysaccharides, nylon or nitrocellulose, resins, silica or silica-based materials including silicon and modified silicon, carbon, metals, inorganic glasses, optical fiber bundles, and a variety of other polymers. In one embodiment, the solid support is flat. In one embodiment, the solid support is a bead (e.g., Spherical silica beads, Inorganic nanoparticles (NPs) of iron oxide (Fe$_3$O$_4$) and metal particles (e.g., gold and silver), magnetic nanoparticles cadmium based dots, and cadmium free dots). Particularly useful solid supports include silica beads and bead arrays such as those described in U.S. Pat. Nos. 6,266,459; 6,355,431; 6,770,441; 6,859,570; 6,210,891; 6,258,568; 6,274,320; U.S. Patent Application Publication Nos. 2009/0026082 A1; 2009/0127589 A1; 2010/0137143 A1; 2010/0282617 A1; or PCT Publication No. WO 00/63437; the entirety of each of which is incorporated herein by reference; or those commercialized in BeadArray™ platforms marketed by Illumina, Inc. (San Diego, CA). Other useful solid supports are those that are used in flow cells. Exemplary flow cells include, but are not limited to, those used in a nucleic acid sequencing apparatus such as flow cells for the NovaSeq®, Genome Analyzer®, MiSeq®, NextSeq® or HiSeq® platforms commercialized by Illumina, Inc. (San Diego, CA); or for the SOLiD™ or Ion Torrent™ sequencing platform commercialized by Life Technologies (Carlsbad, CA). Exemplary flow cells, their compositions and methods for their manufacture and use are also described, for example, in PCT Publication No. WO 2014/142841 A1; U.S. Patent Application Publication No. 2010/0111768 A1; and U.S. Pat. No. 8,951,781; the entirety of each of which is incorporated herein by reference.

In one embodiment, the moiety of R is attached to the solid support. The moiety of R can be an organic moiety (e.g., carbon atom or carbon-containing moiety or amine derivative) or an inorganic moiety (e.g., a silane). In some embodiments, R can be a gel or a linker that is attached to a gel. The gel can, in turn, be attached to the solid support, for example, via covalent bonding or non-covalent association. Useful gels include, but are not limited to hydrogels such as acrylamide, methacrylamide, hydroxyethyl methacrylate, N-vinyl pyrolidinone or derivatives thereof. In some embodiments, the gel can include two or more different species of compound that form a co-polymer. For example, two or more different species of acrylamide, methacrylamide, hydroxyethyl methacrylate, N-vinyl pyrolidinone or derivatives thereof can function as co-monomers that polymerize to form a copolymer hydrogel. Useful hydrogels include, but are not limited to, silane-free acrylamide (SFA) polymer (see, e.g., U.S. Patent Application Publication No. 2011/0059865 A1, the entirety of which is incorporated herein by reference), poly(N-(5-azidoacetamidylpentyl)acrylamide-co-acrylamide) (PAZAM) (see, e.g., U.S. Pat. No. 9,012,022, the entirety of which is incorporated herein by reference), polyacrylamide polymers formed from acrylamide and an acrylic acid or an acrylic acid containing a vinyl group as described, for example, in PCT Publication No. WO 00/31148, the entirety of which is incorporated herein by reference; polyacrylamide polymers formed from monomers that form [2+2] photo-cycloaddition reactions, for example, as described in PCT Publication Nos. WO 01/01143 or WO 03/014392, the entirety of each of which is incorporated herein by reference; or polyacrylamide copolymers as described, for example, in U.S. Pat. No. 6,465,178, PCT Publication Nos. WO 01/62982 and WO 00/53812, the entirety of each of which is incorporated herein by reference.

In one embodiment, the moiety of R is attached to the solid support via a linker. In one embodiment, the linker comprises one or more linker units selected from the group consisting of mono-hydrazinyl-1,3,5-triazine, di-hydrazinyl-1,3,5-triazine or hydrazinecarboxamide. In one embodiment, the linker comprises one linker unit. In one embodiment, the linker comprises two linker units. In one embodiment, the linker comprises three or more linker units. The multiple linker units in a linker can be identical or different. In some embodiments, a linker comprises one or more functional groups such as alkyl, heteroalkyl (e.g., polyethylene glycol), peptide, silanes, alkoxysilanes, or other suitable linker groups. In some embodiments, the linker is —OSi(OZ)$_2$— or —OSi(OZ)$_2$-alkyl-(NH)$_{0-1}$, where Z is as defined above. In other embodiments, the linker is —OSi(OZ)$_2$-propyl- or —OSi(OZ)$_2$-propyl-NH—.

In one embodiment, the compound of R—NHNH$_2$ is attached to a solid support, and together with the solid support comprises a compound of one of following structures (or tautomers thereof):

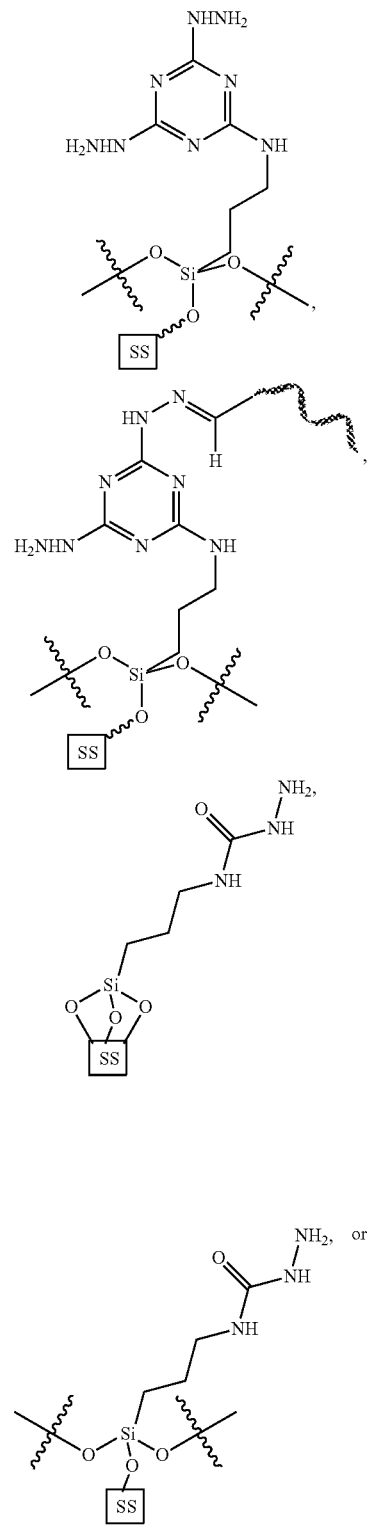

-continued

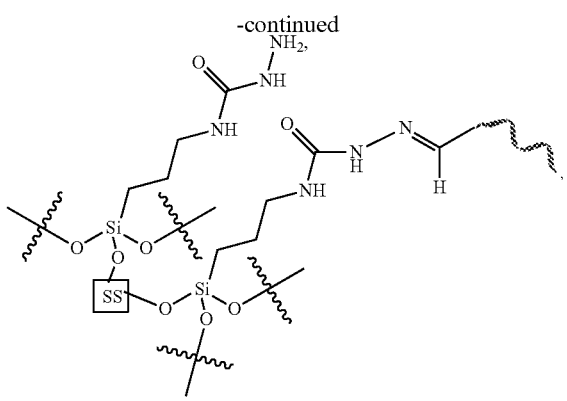

wherein the strand moiety is a nucleic acid molecule, such as DNA. The wave lines in the structures indicate open linkage to adjacent molecules or H or alkyl groups. [SS] in the structures indicates a solid support. In some embodiments, R—NHNH$_2$ is attached to a solid support, and together with the solid support and optional linker comprises: [SS]—OSi(OZ)$_2$-alkyl-NHC(O)NHNH$_2$, wherein Z is alkyl, H, or a silicon atom of an adjacent solid support-bound group. In some embodiments, each alkyl is independently C$_{2-6}$alkyl.

In one embodiment, provided herein is a process for preparing a compound of Formula (II):

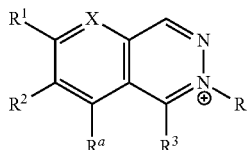

(II)

comprising reacting a compound of Formula (III):

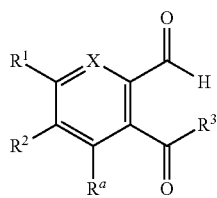

(III)

with a compound of R—NHNH$_2$,
wherein
X is CR$^a$ or N,
R$^1$ and R$^2$ are R$^a$; or R$^1$ and R$^2$ together with the carbon atoms they are attached to form a monocyclic or multicyclic fused aryl or heteroaryl ring, which is optionally substituted with one or more R$^{a1}$;
R$^3$ is hydrogen, alkyl, cycloalkyl, heterocyclyl, aryl, or heteroaryl; each of which is optionally substituted with one or more R$^b$;
R is optionally substituted aryl or heteroaryl;
each instance of R$^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$;
each instance of R$^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$; and
each instance of R$^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, X is CR$^a$. In one embodiment, provided herein is a process for preparing a compound of Formula (II-a):

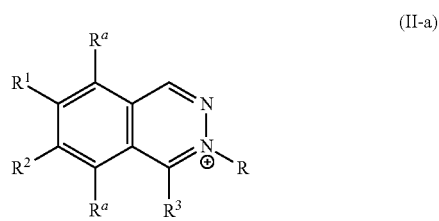

(II-a)

comprising reacting a compound of Formula (III-a):

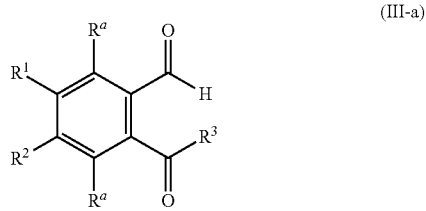

(III-a)

with a compound of R—NHNH$_2$,
wherein:
R$^1$ and R$^2$ are R$^a$; or R$^1$ and R$^2$ together with the carbon atoms they are attached to form a monocyclic or multicyclic fused aryl or heteroaryl ring, which is optionally substituted with one or more R$^{a1}$;
R$^3$ is hydrogen, alkyl, cycloalkyl, heterocyclyl, aryl, or heteroaryl; each of which is optionally substituted with one or more R$^b$;
R is optionally substituted aryl or heteroaryl;
each instance of R$^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$;
each instance of R$^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and
each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, X is N. In one embodiment, provided herein is a process for preparing a compound of Formula (II-b):

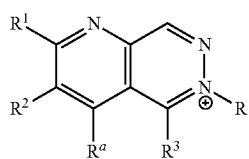

(II-b)

comprising reacting a compound of Formula (III-b):

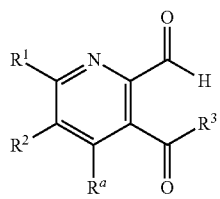

(III-b)

with a compound of R—NHNH$_2$,
wherein:
$R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;
$R^3$ is hydrogen, alkyl, cycloalkyl, heterocyclyl, aryl, or heteroaryl; each of which is optionally substituted with one or more $R^b$;
R is optionally substituted aryl or heteroaryl;
each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;
each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and
each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, R is optionally substituted alkyl, cycloalkyl, heterocyclyl, aryl, or heteroaryl. In one embodiment, R is optionally substituted alkyl, aryl, or heteroaryl. In some embodiments, R is optionally substituted with one or more substituents independently selected from the group consisting of alkyl, halo, chloro, hydroxyl, amino, hydrazino, alkoxy, cyano, amido, carboxyl, —NHC(O)NHNH$_2$, —NHC(O)NH—N═C(H)-oligonucleotide, and —NH—N═C(H)-oligonucleotide. In some embodiments, R is optionally substituted with or more substituents independently selected from the group consisting of chloro, amino, hydrazine, and —NH—N═C(H)-oligonucleotide. In such embodiments, the oligonucleotide portion of —NH—N═C(H)-oligonucleotide is the condensation product of an oligonucleotide with an aldehyde substituent and a hydrazine moiety.

In one embodiment, R is optionally substituted alkyl. In further embodiments, R is optionally substituted $C_{2-10}$alkyl or $C_{2-6}$alkyl or $C_{3-5}$alkyl or propyl. In further embodiments, R is $C_{2-10}$alkyl or $C_{2-6}$alkyl or $C_{3-5}$alkyl or propyl.

In one embodiment, R is optionally substituted aryl. In one embodiment, R is optionally substituted phenyl.

In one embodiment, R is optionally substituted 5- or 6-membered monocyclic heteroaryl. In one embodiment, R is optionally substituted pyrimidyl. In one embodiment, R is optionally substituted triazinyl. In some embodiments, R is triazinyl, optionally substituted with one or more substituents as described above. In some embodiments, R is triazinyl, optionally substituted with one or more substituents selected from the group consisting of chloro, hydrazino, —NHC(O)NHNH$_2$, —NHC(O)NH—N═C(H)-oligonucleotide, and —NH—N═C(H)-oligonucleotide.

In one embodiment, R is optionally substituted 9- or 10-membered bicyclic fused heteroaryl. In one embodiment, R is optionally substituted purinyl.

In one embodiment, the compound of R—NHNH$_2$ is 4,6-dihydrazinyl-N-(3-(trimethoxysilyl)propyl)-1,3,5-triazin-2-amine. In one embodiment, the compound of R—NHNH$_2$ is N-(2-(trimethoxysilyl)ethyl)hydrazinecarboxamide. In other embodiments, the compound of R—NHNH$_2$ is triazine substituted with hydrazine and optionally further substituted with one or more of amino, alkylamino, hydrazino, or —NH—N═C(H)-oligonucleotide. In other embodiments, the compound of R—NHNH$_2$ is triazine substituted with —NHC(O)NHNH$_2$ and optionally further substituted with one or more of amino, alkylamino, —NHC(O)NHNH$_2$, or —NHC(O)NHN═C(H)-oligonucleotide.

In one embodiment, the reaction between the compound of Formula (III) and R—NHNH$_2$ occurs a mildly basic condition. In one embodiment, the mildly basic condition has a pH of from about 9 to about 10.

In one embodiment, the reaction between the compound of Formula (III) and R—NHNH$_2$ occurs in a solvent. In one embodiment, the solvent comprises a buffer solution. In one embodiment, the solvent is a mixture of a water miscible solvent and a buffer solution. In one embodiment, the solvent is a mixture of an alcohol and a buffer solution. In one embodiment, the alcohol is methanol. In another embodiment, the alcohol is ethanol. In one embodiment, the buffer solution is a borate buffer solution. In another embodiment, the buffer solution is a phosphate buffer solution.

In one embodiment, the solvent is a mixture (e.g., about 1:1 mixture) of methanol and borate buffer (e.g., about pH 9-10). In one embodiment, the solvent is a mixture (e.g., about 1:1 mixture) of ethanol and borate buffer (e.g., about pH 9-10).

In one embodiment, the reaction between the compound of Formula (III) and R—NHNH$_2$ achieves substantial completion from about 1 minute to about 6 hours. In one embodiment, the reaction between the compound of Formula (III) and R—NHNH$_2$ achieves at least 50%, at least 60%, at least 70%, at least 80%, at least 85%, at least 90%, at least 95%, at least 97.5%, at least 99%, at least 99.5%, or at least 99.9% yield within about 6 hours, about 4 hours, about 2 hours, about 1 hour, about 30 minutes, about 15 minutes, about 10 minutes, or about 5 minutes. In one embodiment, the reaction between the compound of Formula (III) and R—NHNH$_2$ achieves at least 70% yield within about 1 hour. In one embodiment, the reaction between the compound of Formula (III) and R—NHNH$_2$ achieves at least 90% yield within about 1 hour. In one embodiment, the reaction between the compound of Formula (III) and R—NHNH$_2$ achieves at least 70% yield within about 30 minutes. In one embodiment, the reaction between the compound of Formula (III) and R—NHNH$_2$ achieves at least 90% yield within about 30 minutes.

In some embodiments, X is CR$^a$. In other embodiments, X is N.

In one embodiment, R$^1$ and R$^2$ are R$^a$.

In one embodiment, R$^1$ and R$^2$ together with the carbon atoms they are attached to form a monocyclic aryl ring. In one embodiment, R$^1$ and R$^2$ together with the carbon atoms they are attached to form an optionally substituted phenyl ring.

In one embodiment, R$^1$ and R$^2$ together with the carbon atoms they are attached to form an optionally substituted monocyclic heteroaryl ring.

In one embodiment, R$^1$ and R$^2$ together with the carbon atoms they are attached to form a bicyclic fused aryl ring. In one embodiment, R$^1$ and R$^2$ together with the carbon atoms they are attached to form an optionally substituted naphthyl ring.

In one embodiment, R$^3$ is hydrogen, alkyl, aryl, or heteroaryl.

In one embodiment, R$^3$ is hydrogen.
In one embodiment, R$^3$ is alkyl.
In one embodiment, R$^3$ is phenyl.

In one embodiment, the compound of Formula (III) is:

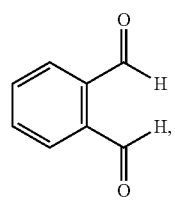
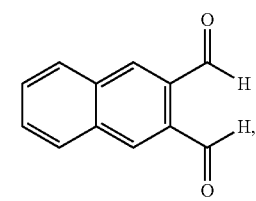
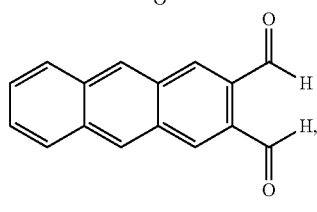
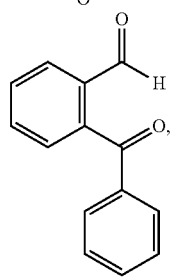
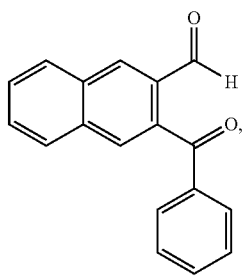
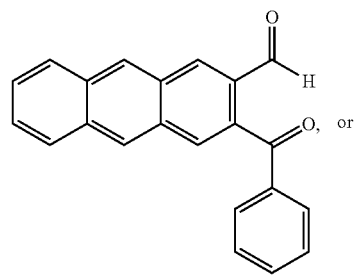
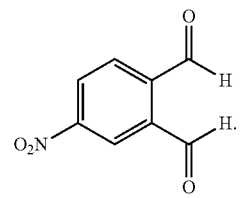

In one embodiment, the compound of Formula (III) is

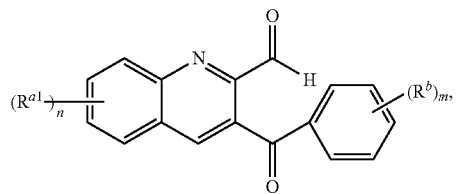

wherein n is 0, 1, 2, 3, or 4; and m is 0, 1, 2, 3, or 4.

In one embodiment, n is 0. In one embodiment, n is 1. In one embodiment, n is 2. In one embodiment, n is 3. In one embodiment, n is 4.

In one embodiment, m is 0. In one embodiment, m is 1. In one embodiment, m is 2. In one embodiment, m is 3. In one embodiment, m is 4.

In one embodiment, the compound of Formula (III) is

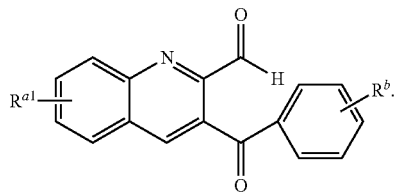

In one embodiment, the compound of Formula (III) is

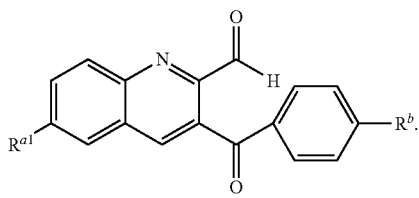

In some embodiments, each instance of $R^a$ is independently hydrogen, halo, cyano, alkyl, hydroxyl, or alkoxy. In other embodiments, each instance of $R^a$ is hydrogen.

In one embodiment, each instance of $R^{a1}$ is independently halogen, or a carbon or nitrogen based functional group. In one embodiment, each instance of $R^a$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, acyl, acyloxy, or alkoxycarbonyl. In other embodiments, each instance of $R^{a1}$ is independently halogen, alkyl, hydroxyl, alkoxy, cyano, amido, carboxyl, acyl, acyloxy, or alkoxycarbonyl. In still other embodiments, each instance of $R^{a1}$ is independently halogen, alkyl, hydroxyl, alkoxy, or cyano.

In one embodiment, each instance of $R^b$ is independently halogen, or a carbon or nitrogen based functional group. In one embodiment, each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, acyl, acyloxy, or alkoxycarbonyl. In other embodiments, each instance of $R^b$ is independently halogen, alkyl, hydroxyl, alkoxy, cyano, amido, carboxyl, acyl, acyloxy, or alkoxycarbonyl. In still other embodiments, each instance of $R^b$ is independently halogen, alkyl, hydroxyl, alkoxy, carboxyl, or cyano.

In one embodiment, the compound of Formula (III) is

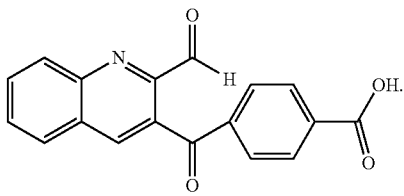 [SMILES: O=Cc1nc2ccccc2cc1C(=O)c1ccc(C(=O)O)cc1]

In one embodiment, without being limited by a particular theory, a compound of Formula (I) provided herein exhibits fluorescent signal. In one embodiment, a compound of Formula (I) provided herein exhibits fluorescent signal at a wavelength of from about 400 nm to about 600 nm. In one embodiment, a compound of Formula (I) provided herein exhibits fluorescent signal in an acidic condition. In one embodiment, the acidic condition has a pH of from about 2 to about 4. In one embodiment, the intensity of the signal is proportional to the concentration of the compound of Formula (I).

In one embodiment, without being limited by a particular theory, a compound of Formula (II) provided herein exhibits fluorescent signal. In one embodiment, a compound of Formula (II) provided herein exhibits fluorescent signal at a wavelength of from about 400 nm to about 600 nm. In one embodiment, a compound of Formula (II) provided herein exhibits fluorescent signal in an acidic condition. In one embodiment, the acidic condition has a pH of from about 2 to about 4. In one embodiment, the intensity of the signal is proportional to the concentration of the compound of Formula (II).

In one embodiment, provided herein is a method for assaying a compound of R—$NH_2$, comprising (i) reacting a sample containing the compound with a compound of Formula (III) in the presence of a cyanide ion to form a compound of Formula (I), and (ii) detecting and measuring the fluorescence of the compound of Formula (I).

In one embodiment, provided herein is a method for assaying a compound of R—$NH_2$, comprising the steps of
(i) reacting a sample containing a compound of R—$NH_2$ with a compound of Formula (III):

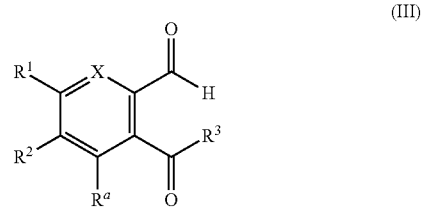

in the presence of a cyanide ion to form a compound of Formula (I):

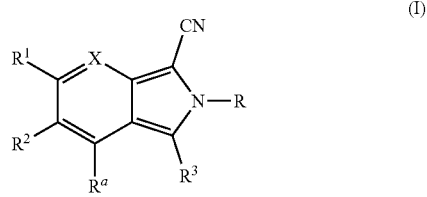

and (ii) detecting and measuring the fluorescence of the compound of Formula (I);
wherein:
  X is $CR^a$ or N,
  $R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;
  $R^3$ is hydrogen, alkyl, cycloalkyl, heterocyclyl, aryl, or heteroaryl; each of which is optionally substituted with one or more $R^b$;
  R is a moiety, which is attached to a solid support directly or via a linker;
  each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;
  each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, provided herein is a method for assaying a compound of R—NH$_2$, comprising the steps of (i) reacting a sample containing a compound of R—NH$_2$ with a compound of Formula (III):

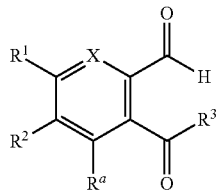

in the presence of a cyanide ion to form a compound of Formula (I):

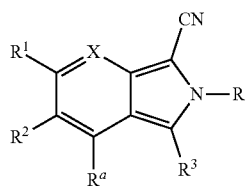

and (ii) detecting and measuring the fluorescence of the compound of Formula (I);

wherein:

X is $CR^a$ or N, $R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;

$R^3$ is hydrogen, alkyl, cycloalkyl, heterocyclyl, aryl, or heteroaryl; each of which is optionally substituted with one or more $R^b$;

R is optionally substituted heteroaryl;

each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;

each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, R is not 2-pyridyl or 3-pyridyl.

In one embodiment, provided herein is a method for assaying a compound of R—NHNH$_2$, comprising (i) reacting a sample containing the compound with a compound of Formula (III) to form a compound of Formula (II), (ii) optionally adjusting the pH to a suitable value, and (iii) detecting and measuring the fluorescence of the compound of Formula (II).

In one embodiment, provided herein is a method for assaying a compound of R—NHNH$_2$, comprising the steps of (i) reacting a sample containing a compound of R—NHNH$_2$ with a compound of Formula (III):

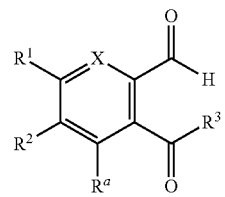

to form a compound of Formula (II):

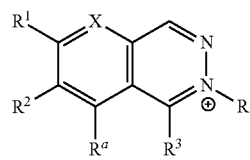

(ii) optionally adjusting the pH to a suitable value;

and (iii) detecting and measuring the fluorescence of the compound of Formula (I);

wherein:

X is $CR^a$ or N, $R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;

$R^3$ is hydrogen, alkyl, cycloalkyl, heterocyclyl, aryl, or heteroaryl; each of which is optionally substituted with one or more $R^b$;

R is a moiety, which is attached to a solid support directly or via a linker;

each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;

each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, provided herein is a method for assaying a compound of R—NHNH$_2$, comprising the steps of (i) reacting a sample containing a compound of R—NHNH$_2$ with a compound of Formula (III):

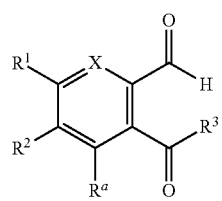

(III)

to form a compound of Formula (II):

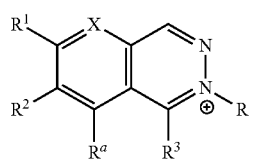

(II)

(ii) optionally adjusting the pH to a suitable value;
and (iii) detecting and measuring the fluorescence of the compound of Formula (I);
wherein:
X is $CR^a$ or N,
$R^1$ and $R^2$ are $R^a$; or $R^1$ and $R^2$ together with the carbon atoms they are attached to form a monocyclic or multicyclic fused aryl or heteroaryl ring, which is optionally substituted with one or more $R^{a1}$;
$R^3$ is hydrogen, alkyl, cycloalkyl, heterocyclyl, aryl, or heteroaryl; each of which is optionally substituted with one or more $R^b$;
R is optionally substituted aryl or heteroaryl;
each instance of $R^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$;
each instance of $R^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more $R^b$; and each instance of $R^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy.

In one embodiment, the suitable pH value in step (ii) is from about 1 to about 4. In one embodiment, the pH is about 3. Without being bound by a particular theory, the following exemplary reaction may occur while adjusting the pH to acidic:

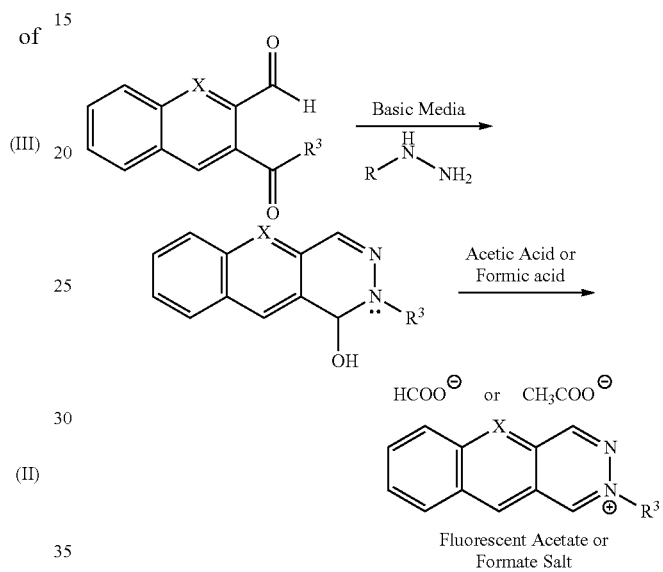

In one embodiment, the assaying methods provided herein can be used for quality assessment of solid supports being made or used in particular applications. By way of non-limiting example, an application of the methods to quality control of bead manufacturing is set forth below. Those skilled in the art will understand that the methods can be similarly applied to evaluation and characterization of other solid supports. In one embodiment, the quality control is conducted stepwise.

In one embodiment, the initial density of —NH$_2$ group in a bead material is determined by an assaying method provided herein. The —NH$_2$ group is then converted to a different function group, and the remaining amount of the —NH$_2$ group is optionally determined by an assaying method provided herein. The functional group is then converted to —NHNH$_2$ group, and the density of the —NHNH$_2$ group in the bead material is determined by an assaying method provided herein. The —NHNH$_2$ group is then converted to a different function group, and the remaining amount of the —NHNH$_2$ group is optionally determined by an assaying method provided herein.

In one embodiment, provided herein is a method of quality control of bead manufacturing, comprising:
(a) providing a material containing a —NH$_2$ group;
(b) optionally determining the density of —NH$_2$ group in the material by reacting the —NH$_2$ group with a compound of Formula (III) provided herein in the presence of a cyanide ion to form a compound of Formula (I) provided herein, and detecting and measuring the fluorescence of the compound of Formula (I);

(c) reacting the —NH$_2$ group with

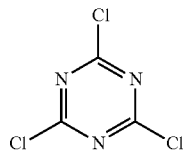

to provide a

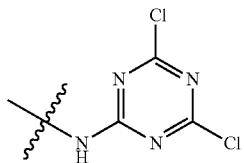 [SMILES: *Nc1nc(Cl)nc(Cl)n1]

group;
(d) optionally determining the remaining amount of the —NH$_2$ group in the material by repeating step (b);
(e) reacting the

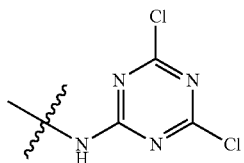

group with hydrazine to provide a

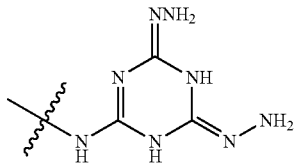

group; and
(f) optionally determining the density of the —NHNH$_2$ group in the material by reacting the —NHNH$_2$ group with a compound of Formula (III) provided herein to form a compound of Formula (II) provided herein, optionally adjusting the pH to a suitable value, and detecting and measuring the fluorescence of the compound of Formula (II).

In one embodiment, the method of quality control further comprises
(g) reacting the

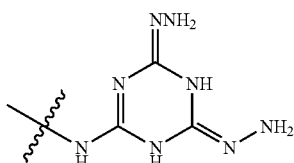

group with an aldehyde containing DNA to provide a

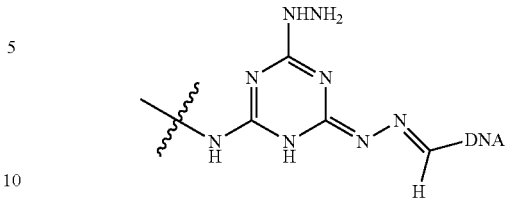

group; and
(h) optionally determining the remaining amount of the —NHNH$_2$ group in the material by repeating step (f).

In one embodiment, at least one determining step of steps (b), (d), (f), and (h) is performed. In one embodiment, at least two determining steps of steps (b), (d), (f), and (h) are performed. In one embodiment, at least three determining steps of steps (b), (d), (f), and (h) are performed. In one embodiment, all four determining steps of steps (b), (d), (f), and (h) are performed.

In one embodiment, the assaying methods provided herein can be used for monitoring the stability of a material (e.g., a solid support material) containing a —NH$_2$ group. In one embodiment, the assaying methods provided herein can be used for monitoring the stability of a material containing a —NHNH$_2$ group. The methods comprise assaying the amount of the —NH$_2$ group or —NHNH$_2$ group in the material over a period of time, wherein a decrease of the amount indicates that the material is not stable over the period of time.

In one embodiment, the assaying methods provided herein can be used for determining the concentration of a DNA molecule in a sample. In one embodiment, the assaying methods provided herein are used to detect subnanomolar per milligram concentration of a DNA molecule in a sample indirectly through —NHNH$_2$ group determination.

In one embodiment, the assaying methods provided herein can be used for distinguishing different —NH$_2$ groups or —NHNH$_2$ groups, based on the difference in the reaction speed, and/or the intensity and wavelength of the fluorescent signal.

EXAMPLES

Certain embodiments provided herein are illustrated by the following non-limiting examples.

As depicted in the Examples below, in certain exemplary embodiments, compounds are prepared according to the following general procedures. It will be appreciated that, although the general methods depict the synthesis of certain compounds of the present disclosure, the following general methods, and other methods known to one of ordinary skill in the art, can be applied to all compounds and subclasses and species of each of these compounds, as described herein.

In the illustrative examples that follow, reactions were carried out at room or ambient temperature, in the range of 18-25° C. unless otherwise stated. Organic solutions were dried over anhydrous magnesium sulfate or sodium sulfate and evaporation of solvent was carried out using a rotary evaporator under reduced pressure. In general, the courses of reactions were followed by TLC or LCMS and reaction times are representative. Yields are given for illustration only and are not necessarily those which can be obtained by diligent process development.

Example 1. Reaction with Amino Containing Material

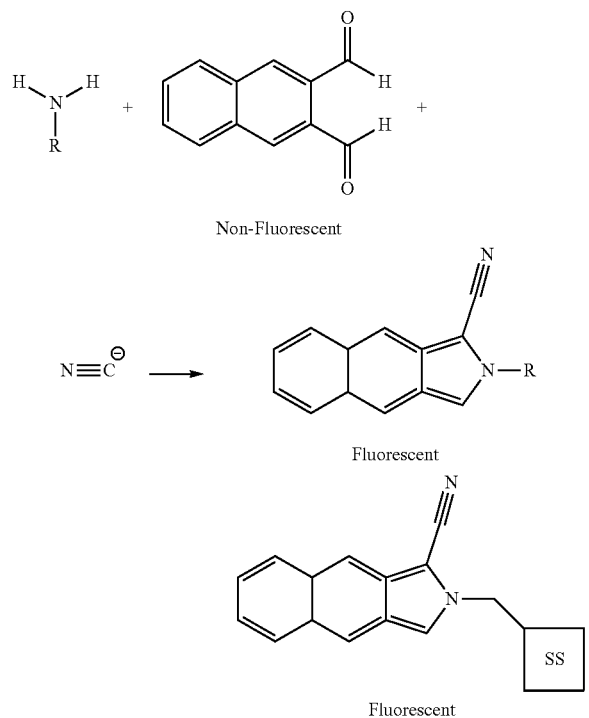

Example 2. Reaction with Hydrazine Containing Material

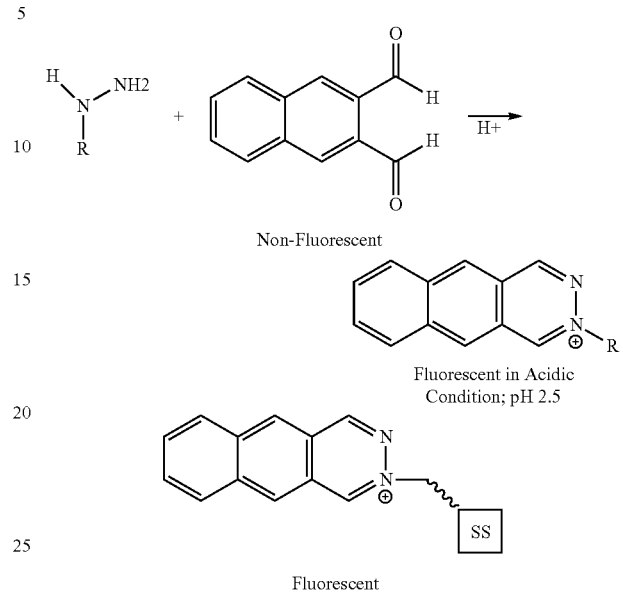

20 milligrams of dried amino containing bead sample from the corresponding manufacturing step was dissolved in 1 mL methanol. 1 mL 0.05M sodium borate buffer (pH 9.5), 0.5 mL sodium cyanide reagent, and 0.5 mL NDA reagent were added, exactly in the sequence given. The vial was sealed with teflon-lined screw cap and stirred for 15 min at RT. 25 microliter of the NDA derivatization solution was then diluted with 1 mL 0.05 M phosphate buffer (pH 7)-Methanol (40+60, v/v). Linear fluorescent response of NDA derivative was determined at 420 nm (excitation) and 480 nm (emission) with a xenon bulb pulse rate of 100 pulses/s.

50 microliter of the amine (e.g., hexyl amine) mother liquor was dissolved into 0.95 mL methanol. 1 mL 0.05 M sodium borate buffer (pH 9.5), 0.5 mL sodium cyanide reagent, and 0.5 mL NDA (4 mg in 8 mL methanol) reagent were added, exactly in the sequence given. The vial was sealed with teflon-lined screw cap and stirred for 20 min at RT. 25 microliter of the NDA derivatization solution was then diluted with 1 mL 0.05M phosphate buffer (pH 7)-Methanol (40+60, v/v). Linear fluorescent response of NDA derivative was determined at 420 nm (excitation) and 490 nm (emission) with a xenon bulb pulse rate of 100 pulses/s for different concentrations of amine (e.g., hexyl amine).

Figure 2:
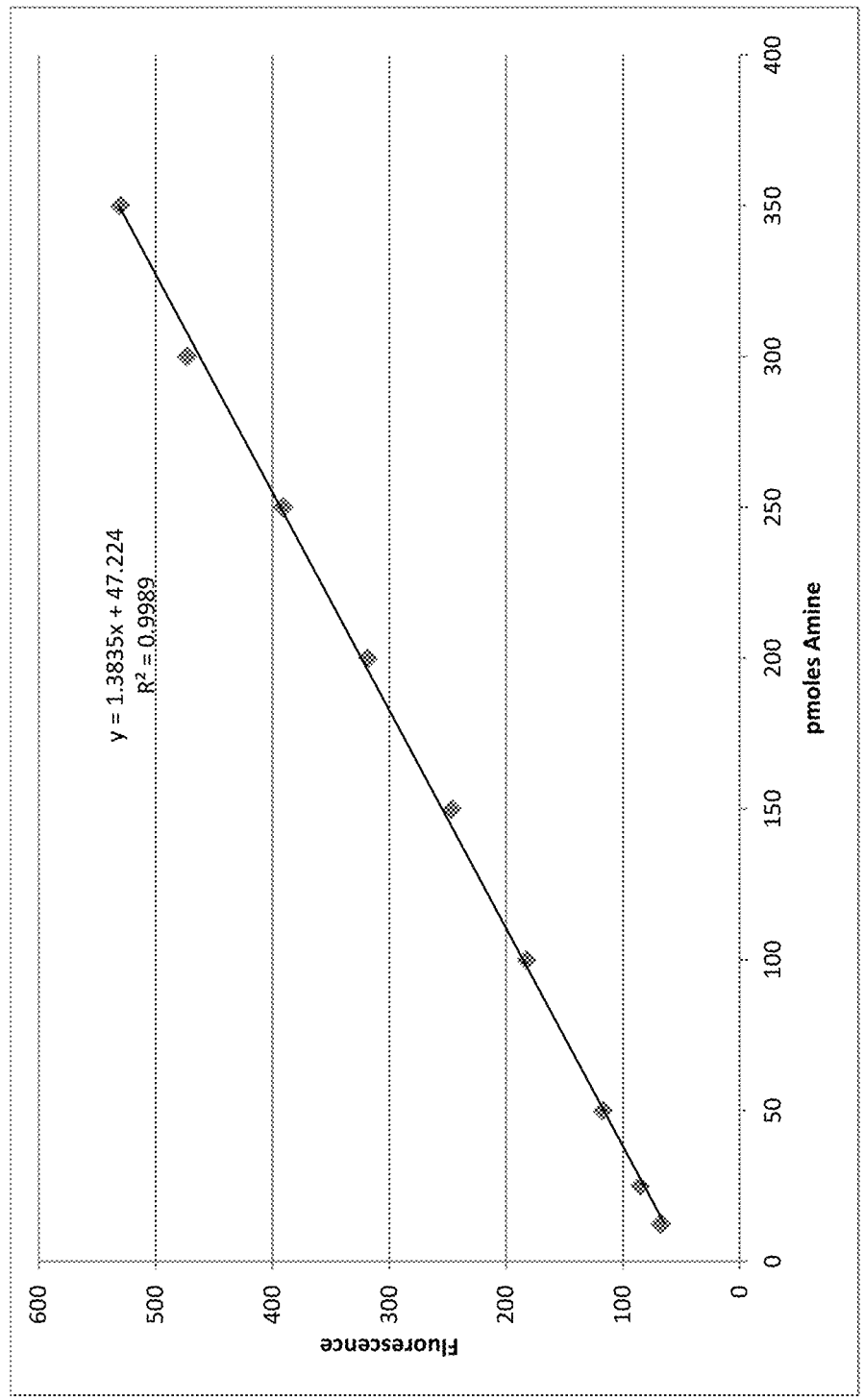
FIG. 2 shows linear calibration of a typical fluorescence emission of a product of Formula (I).

The linear calibration curve was drawn. The detection limit was sub-nanomolar concentrations of hexyl amine per milligrams of silica beads. A typical fluorescence emission spectrum is shown in FIG. 1 ($\lambda_{ex}$=419 nm and $\lambda_{em}$=480 nm). A typical fluorescence emission linear calibration of a product of Formula (I) is shown in FIG. 2.

The highly chemo-selective reaction of hydrazinotriazine with 2,3-naphthalene dicarboxaldehyde followed by fluorescence emission $\lambda_{ex}$=400 nm) is utilized for ultra-sensitive quantification of hydrazine-triazine moiety on the Illumina's bead in the bead manufacture. The adduct is fluorescent in the mild acidic condition (e.g., in acetic acid) as the protonated 2-methylbenzo[g]phthalazin-2-ium is highly fluorescent while being excited at 320 nm or 400 nm (reaction time response<10 min, $\lambda_{ex}$=400 nm and $\lambda_{em}$=495 nm). The chemoselectively of the 2,3-naphthalene dicarboxaldehyde reagent is inspected with respect to possible amino functionality (standard 1 mM solution of 6-hydrazinyl-N2,N4-dipropyl-1,3,5-triazine-2,4-diamine was utilized as a model compound for calibration) and is shown to be a highly specific reagent for hydrazinotriazine.

20 milligrams of dried hydrazine containing bead sample was dissolved from the corresponding manufacturing step in 1 mL methanol. 1 mL 0.05M sodium borate buffer (pH 9.5), and 0.5 mL NDA (4 mg in 8 mL methanol) reagent were added, exactly in the sequence given. The vial was sealed with teflon-lined screw cap, and stirred for 20 min at RT. 50 microliter of the NDA derivatization solution was then diluted with 1 mL of glacial acetic acid. Linear fluorescent response of NDA derivative was determined at 400 nm (excitation) and 490 nm (emission) with a xenon bulb pulse rate of 100 pulses/s.

50 microliter of the hydrazine (e.g., 6-hydrazinyl-N2,N4-dipropyl-1,3,5-triazine-2,4-diamine) mother liquor was dissolved into 0.95 mL methanol. 1 mL 0.05M sodium borate buffer (pH 9.5) and 0.5 mL NDA reagent were added, exactly in the sequence given. Linear fluorescent response of NDA derivative was determined at 400 nm (excitation) and 490 nm (emission) with a xenon bulb pulse rate of 100 pulses/s for different concentrations of hydrazine (e.g., 6-hydrazinyl-N2,N4-dipropyl-1,3,5-triazine-2,4-diamine).

Figure 3:
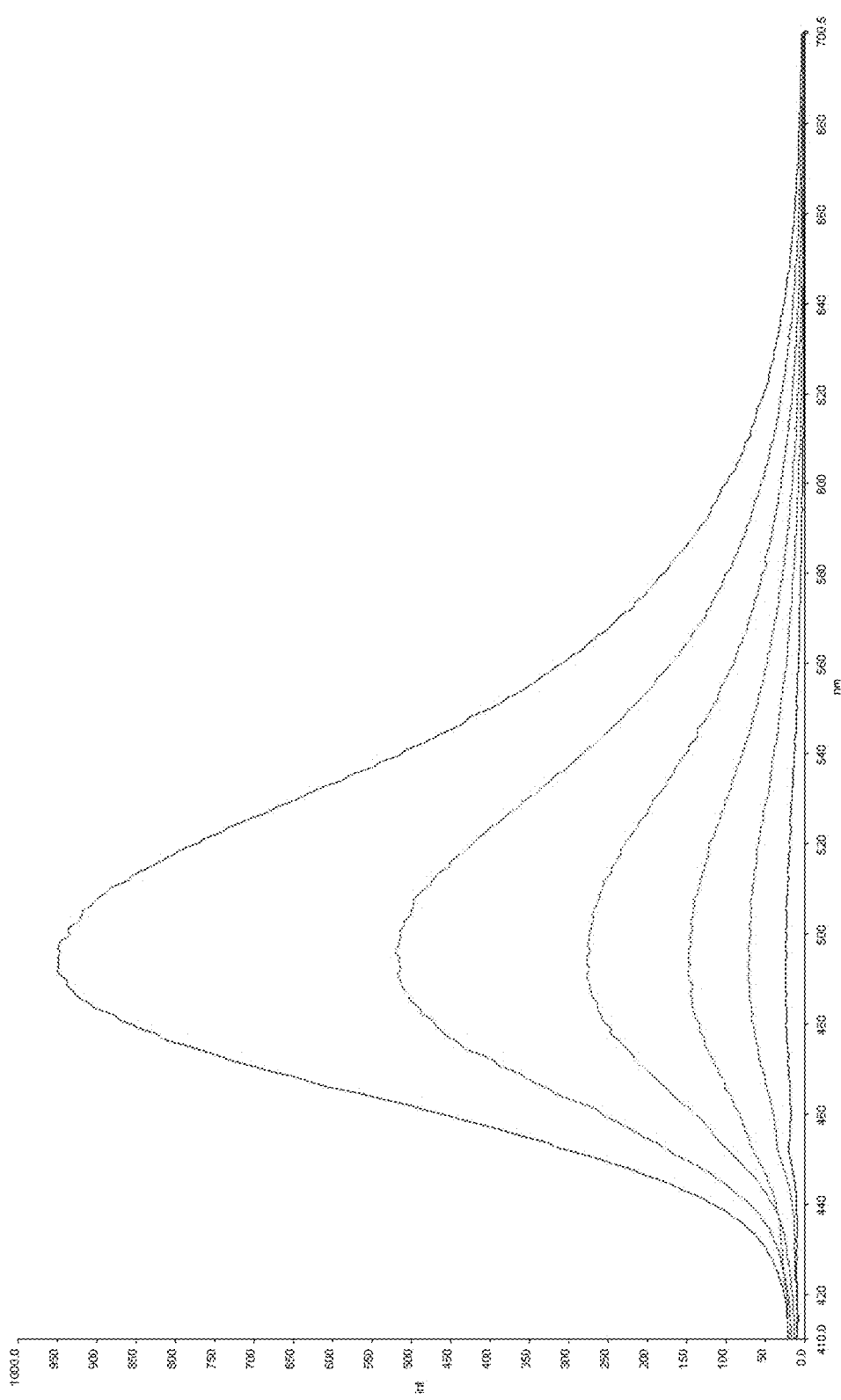
FIG. 3 shows a typical fluorescence emission spectrum of a product of Formula (II).
Figure 4:
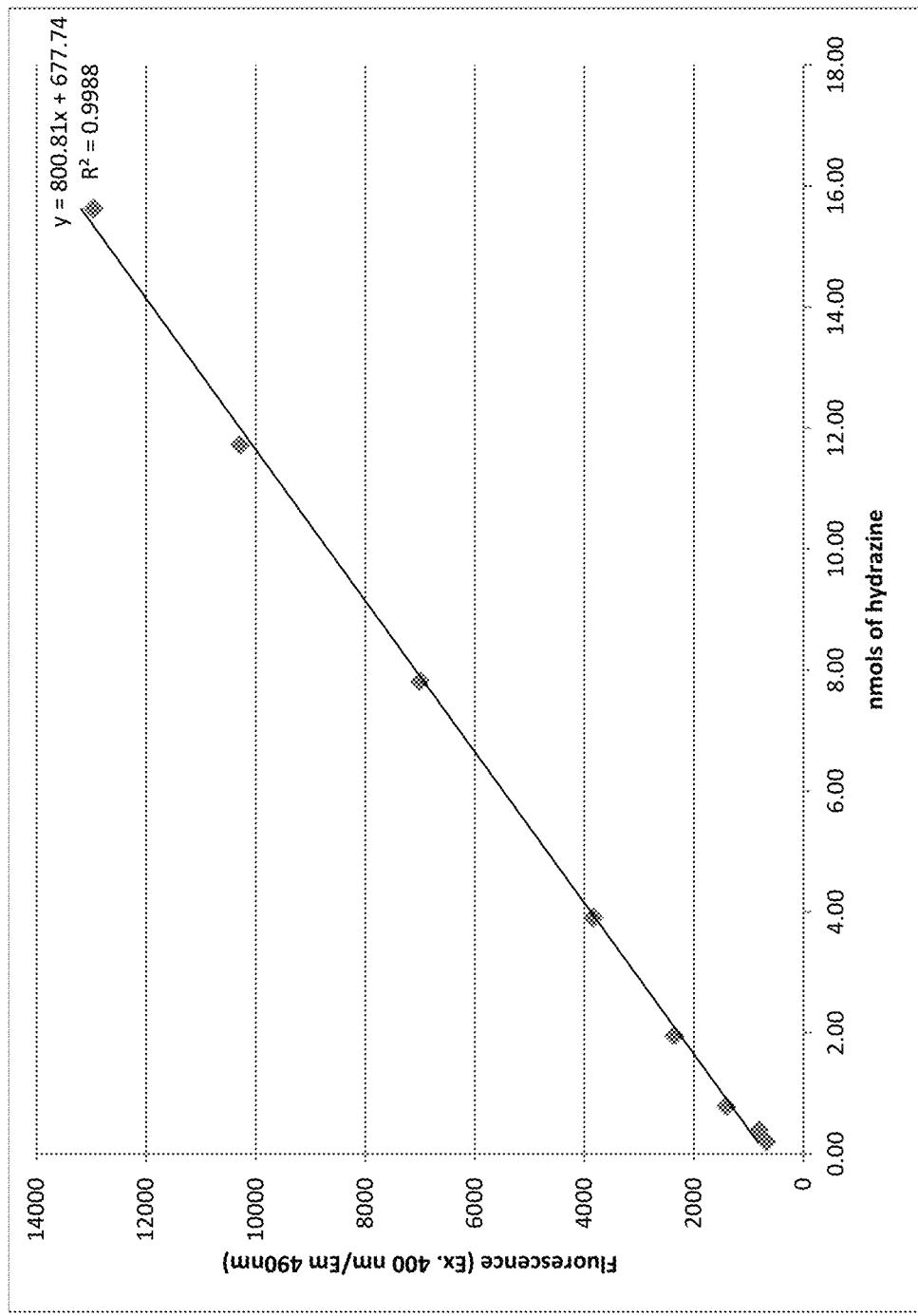
FIG. 4 shows linear calibration of a typical fluorescence emission of a product of Formula (II).

The linear calibration curve was drawn. The detection limit was sub-nanomolar concentrations of hydrazine-triazine per milligrams of silica beads. A typical fluorescence emission spectrum is shown in FIG. 3 ($\lambda_{ex}$=400 nm and $\lambda_{em}$=495 nm). A typical fluorescence emission linear calibration of a product of Formula (II) is shown in FIG. 4.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A process for preparing a compound of Formula (II):

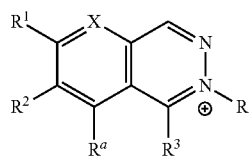

(II)

comprising reacting a compound of Formula (III):

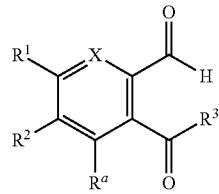

(III)

with a compound of R—NHNH$_2$,
wherein:
X is CR$^a$ or N,
R$^1$ and R$^2$ are R$^a$; or R$^1$ and R$^2$ together with the carbon atoms they are attached to form a monocyclic or multicyclic fused aryl or heteroaryl ring, which is optionally substituted with one or more R$^{a1}$;
R$^3$ is hydrogen, alkyl, cycloalkyl, heterocyclyl, aryl, or heteroaryl; each of which is optionally substituted with one or more R$^b$;
R is a moiety, which is attached to a solid support directly or via a linker;
each instance of R$^a$ is independently hydrogen, halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$;
each instance of R$^{a1}$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more R$^b$;
each instance of R$^b$ is independently halogen, alkyl, alkenyl, alkynyl, heteroalkyl, cycloalkyl, heterocyclyl, aryl, heteroaryl, hydroxyl, alkoxy, cycloalkoxy, heterocyclyloxy, aryloxy, heteroaryloxy, cyano, nitro, amino, amido, carboxyl, sulfonyl, sulfonamido, acyl, acyloxy, alkoxycarbonyl, or phosphate; each of which is optionally substituted with one or more halogen, alkyl, or alkoxy; and wherein the reaction between the compound of Formula (III) and R—NHNH$_2$ occurs under a mildly basic condition.

2. The process of claim 1, wherein R is optionally substituted alkyl, cycloalkyl, heterocyclyl, aryl, or heteroaryl, each of which is attached to the solid support directly or via a linker.

3. The process of claim 1, wherein R is optionally substituted alkyl.

4. The process of claim 1, wherein R is optionally substituted phenyl.

5. The process of claim 1, wherein R is optionally substituted 5- or 6-membered monocyclic heteroaryl, or optionally substituted 9- or 10-membered bicyclic fused heteroaryl.

6. The process of claim 5, wherein R is optionally substituted pyrimidyl, optionally substituted triazinyl, or optionally substituted purinyl.

7. The process of claim 1, wherein R is optionally substituted aminocarbonyl (NH—C=O) or optionally substituted alkylaminocarbonyl (alkyl-NH—C=O), each of which is attached to the solid support directly or via a linker.

8. The process of claim 7, wherein R is C$_{2-6}$alkyl-NHC(O)— or is propyl-NHC(O)—.

9. The process of claim 1, wherein the compound of R—NHNH$_2$ is attached to the solid support, and together with the solid support comprises a compound of one of the following structures, or tautomers thereof:

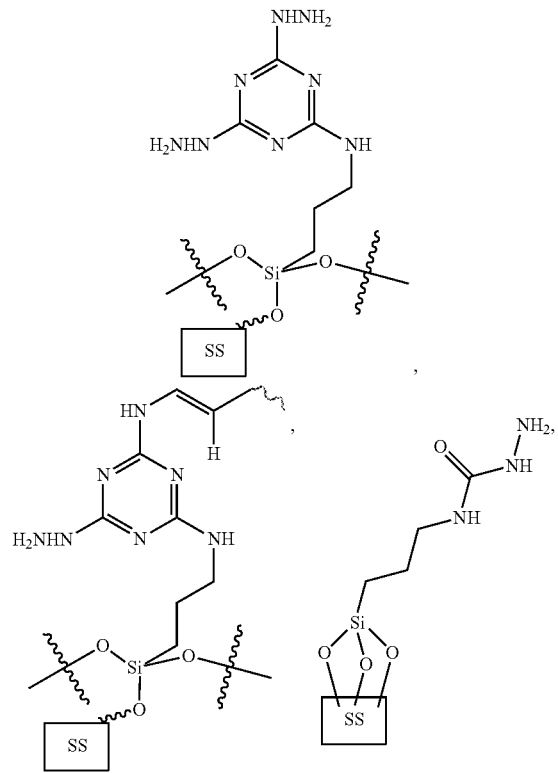

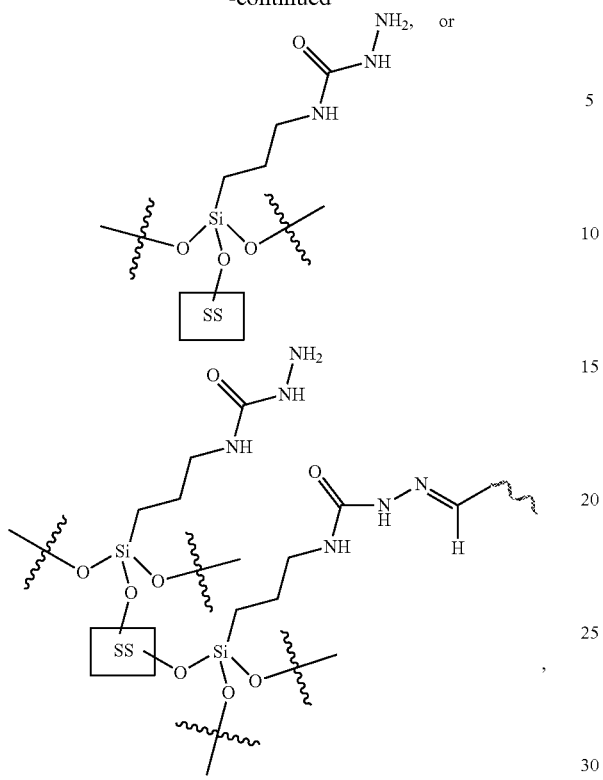

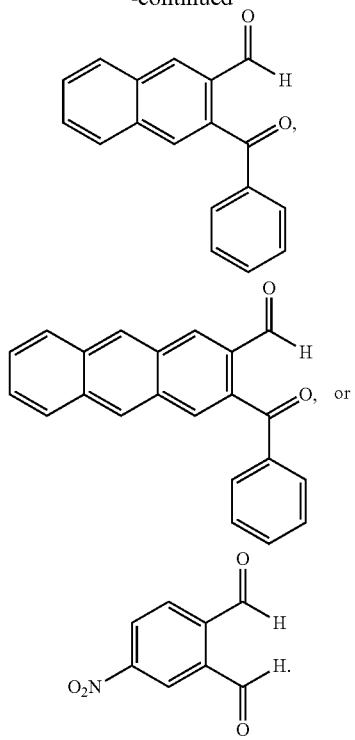

wherein [SS] indicates the solid support and the strand moiety is a nucleic acid molecule.

10. The process of claim 9, wherein the nucleic acid molecule is a DNA.

11. The process of claim 1, wherein $R^1$ and $R^2$ together with the carbon atoms they are attached to form an optionally substituted phenyl ring or optionally substituted naphthalenyl ring.

12. The process of claim 1, wherein $R^1$ and $R^2$ are each $R^a$, and wherein each instance of $R^a$ is independently hydrogen, halo, cyano, alkyl, hydroxyl, or alkoxy.

13. The process of claim 1, wherein $R^3$ is hydrogen, alkyl or phenyl.

14. The process of claim 1, wherein the compound of Formula (III) is:

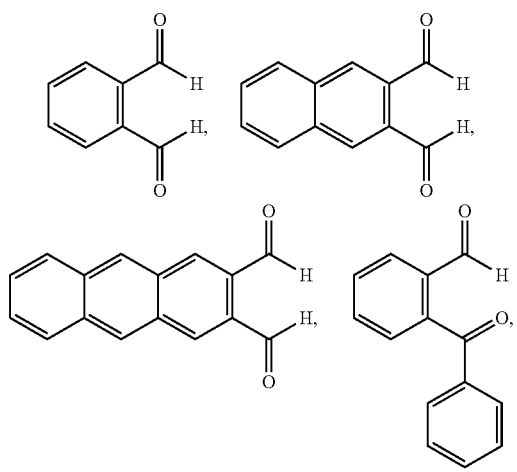

15. The process of claim 1, wherein the compound of Formula (III) is:

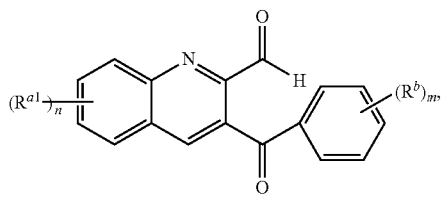

wherein n is 0, 1, 2, 3, or 4; and m is 0, 1, 2, 3, or 4.

16. The process of claim 1, wherein the compound of Formula (III) is:

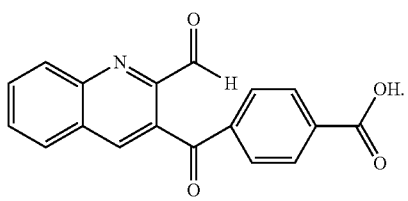 [SMILES: O=Cc1nc2ccccc2cc1C(=O)c1ccc(C(=O)O)cc1]

17. The process of claim 1, wherein the solid support is one or more of glass, modified or functionalized glass, plastics, polysaccharides, nylon, nitrocellulose, resins, silica, silicon, modified silicon, carbon, metals, inorganic glasses, and optical fiber bundles.

18. The process of claim 1, wherein the solid support is a bead.

19. The process of claim 18, wherein the bead is one or more of spherical silica beads, inorganic nanoparticles, magnetic nanoparticles, cadmium based dots, and cadmium free dots.

20. The process of claim 1, further comprising:
   detecting and measuring the fluorescence of the compound of Formula (II) to assay the compound of R—$NHNH_2$.

21. The process of claim 1, wherein the reaction between the compound of Formula (III) and R—$NHNH_2$ occurs at a pH from about 9 to about 10.

22. The process of claim 1, wherein the reaction between the compound of Formula (III) and R—$NHNH_2$ occurs in a mixture of a water miscible solvent and a buffer solution.

* * * * *

UNITED STATES PATENT AND TRADEMARK OFFICE
CERTIFICATE OF CORRECTION

Page 1 of 3

PATENT NO. : 12,060,508 B2
APPLICATION NO. : 18/062492
DATED : August 13, 2024
INVENTOR(S) : Ali Asadi et al.

It is certified that error appears in the above-identified patent and that said Letters Patent is hereby corrected as shown below:

In the Specification

In Column 17, Lines 51-67 (approx.), delete " 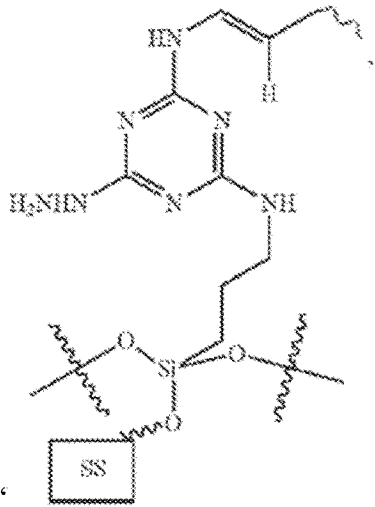 " and insert

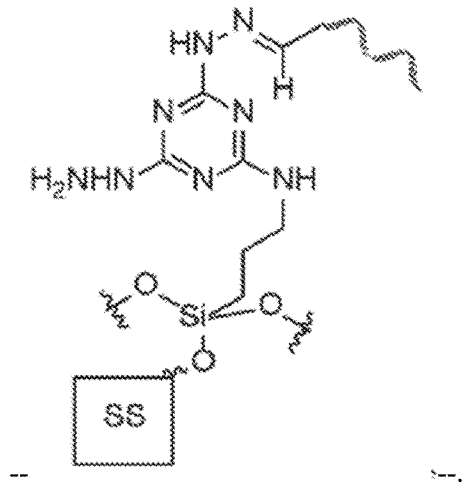

--.

Signed and Sealed this
Twenty-fourth Day of June, 2025

Coke Morgan Stewart
*Acting Director of the United States Patent and Trademark Office*

CERTIFICATE OF CORRECTION (continued)
U.S. Pat. No. 12,060,508 B2

In Column 25, Lines 12-18 (approx.), delete " 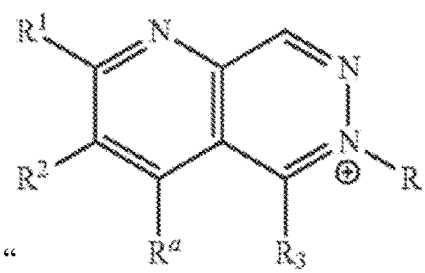 " and insert
-- 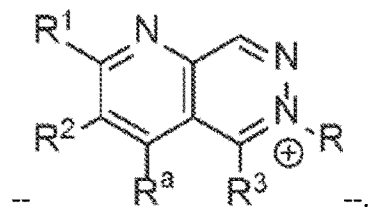 --.

In the Claims

In Column 46, Lines 52-66 (approx.), Claim 9, delete " 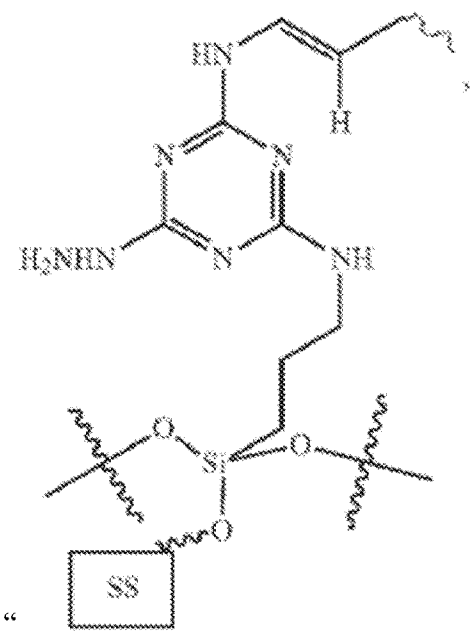 " and insert -- 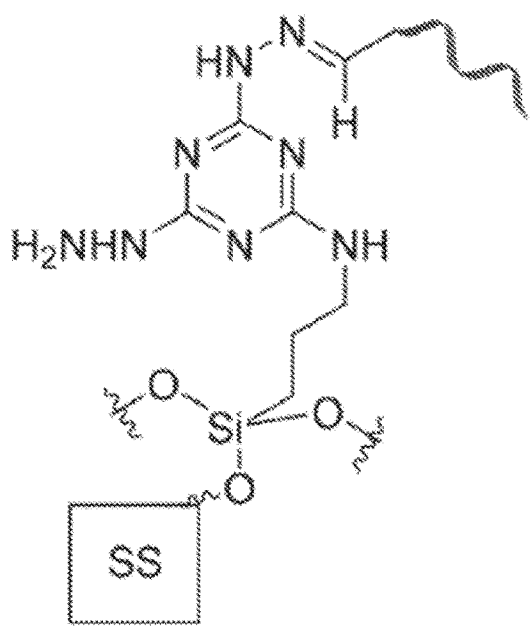 --.